United States Patent [19]

Henle et al.

[11] Patent Number: 5,693,611
[45] Date of Patent: Dec. 2, 1997

[54] CYCLIC PEPTIDE ANTIFUNGAL AGENTS

[75] Inventors: Stacy Kay Henle, Indianapolis; William Wilson Turner, Bloomington, both of Ind.

[73] Assignee: Eli Lilly and Company, Indianapolis, Ind.

[21] Appl. No.: 785,207

[22] Filed: Jan. 17, 1997

Related U.S. Application Data

[60] Provisional application No. 60/010,946 Feb. 1, 1996.
[51] Int. Cl.$^6$ .......................... A61K 38/00; C07C 233/00
[52] U.S. Cl. ........................... 514/9; 564/158; 564/171
[58] Field of Search ............................. 514/9; 564/158, 564/171

[56] References Cited

FOREIGN PATENT DOCUMENTS 0 561 639 A1  9/1993  European Pat. Off. .

*Primary Examiner*—Paula K. Hutzell
*Assistant Examiner*—Benet Prickril
*Attorney, Agent, or Firm*—Daniel W. Collins; David E. Boone

[57] ABSTRACT

Provided are pharmaceutical formulations, and methods of inhibiting fungal and parasitic activity using a compound of formula I

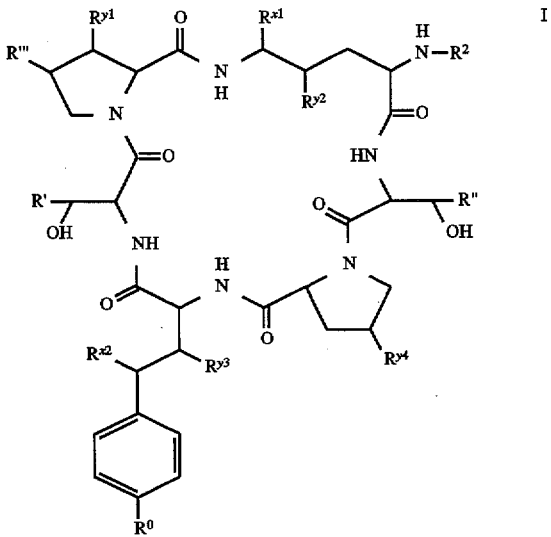

wherein:
R', R'', R''', $R^{x1}$, $R^{x2}$, $R^{y1}$, $R^{y2}$, $R^{y3}$, $R^{y4}$, and $R^0$ are as defined herein below;
$R^2$ is a novel acyl side chain. Also provided are novel formulations and methods of inhibiting fungal and parasitic activity.

30 Claims, No Drawings

CYCLIC PEPTIDE ANTIFUNGAL AGENTS

This application claims the benefit of U.S. provisional application Ser. No. 60/010,946 filed Feb. 1, 1996.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides, to methods for treating fungal and parasitic infections and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin, L-671,329, and S31794/F1.

In general, these cyclic peptides may be characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R^2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula IA where R', R" and R'" are methyl, $R^{x1}$, $R^{x2}$, $R^{y1}$, $R^{y2}$, $R^{y3}$, $R^{y4}$ and $R^0$ are each hydroxy and $R^2$ is p-(octyloxy)benzoyl.

SUMMARY OF THE INVENTION

The present invention provides a compound of formula I wherein:

R' is hydrogen, methyl, —CH$_2$CH$_2$NH$_2$ or —CH$_2$C(O)NH$_2$;

R" and R'" are independently methyl or hydrogen;

$R^{x1}$ is hydrogen, hydroxy, —NH—R, or —O—R;

R is $C_1$-$C_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$_{z2}$, —(CH$_2$)$_c$POR$^{z3}$R$^{z4}$ or —[(CH$_2$)$_2$O]$_d$—(C$_1$-C$_6$)alkyl;

a, b and c are independently 1, 2, 3, 4, 5 or 6;

$R^{z1}$ and $R^{z2}$ are independently hydrogen, $C_1$-$C_6$ alkyl, or $R^{z1}$ and $R^{z2}$ combine to form —CH$_2$(CH$_2$)$_e$CH$_2$—;

$R^{z3}$ and $R^{z4}$ are independently hydroxy or $C_1$-$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —OP(O)(OH)$_2$ or a group of the formula:

$$-O-\overset{O}{\underset{OH}{P}}-R^1 \quad \text{or} \quad -O-\overset{O}{\underset{OH}{P}}-OR^1;$$

$R^1$ is $C_1$-$C_6$ alkyl, phenyl, p-halo-phenyl, p-nitrophenyl, benzyl, p-halo-benzyl or p-nitro-benzyl;

$R^2$ is $$-\overset{O}{\underset{}{C}}-\left(A\right)-X-\left(B\right)-Y-\left(C\right)-R_3;$$

A, B, and C are independently selected from the following groups:

X and Y are independently a bond or —C≡C—;

$R^3$ is $C_1$-$C_{12}$ alkyl, $C_1$-$C_{12}$ alkoxy or —O—(CH$_2$)$_m$—[O—(CH$_2$)$_n$]$_p$—O—(C$_1$-C$_{12}$ alkyl);

m is 2, 3 or 4;

n is 2, 3 or 4; and p is 0 or 1;

with the proviso that A, B, and C cannot all be or a pharmaceutically acceptable salt thereof.

The present invention also provides a compound of formula II

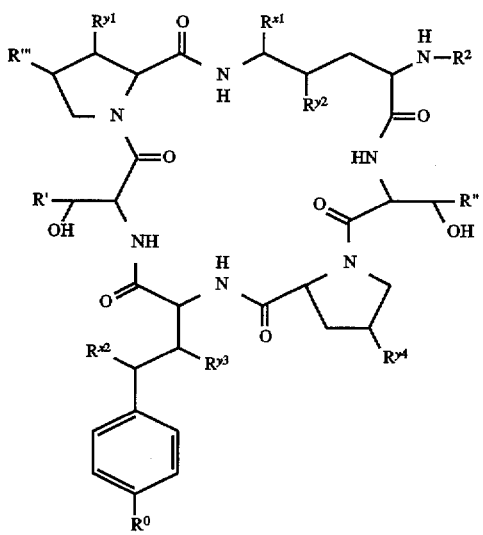

wherein:

R' is hydrogen, methyl or —CH$_2$C(O)NH$_2$;

R" and R'" are independently methyl or hydrogen;

R$^{x1}$ is hydrogen, hydroxy or —O—R;

R is C$_1$–C$_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$)alkyl;

a, b and c are independently 1, 2, 3, 4, 5 or 6;

R$^{z1}$ and R$^{z2}$ are independently hydrogen, C$_1$–C$_6$ alkyl, or R$^{z1}$ and R$^{z2}$ combine to form —CH$_2$(CH$_2$)$_e$CH$_2$—;

R$^{z3}$ and R$^{z4}$ are independently hydroxy or C$_1$–C$_6$ alkoxy;

d is 1 or 2;

e is 1, 2 or 3;

R$^{x2}$, R$^{y1}$, R$^{y2}$, R$^{y3}$ and R$^{y4}$ are independently hydroxy or hydrogen;

R$^0$ is hydroxy, —OP(O)(OH)$_2$ or a group of the formula:

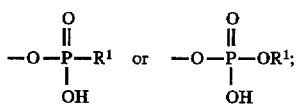

R$^1$ is C$_1$–C$_6$ alkyl, phenyl, p-halo-phenyl, p-nitrophenyl, benzyl, p-halo-benzyl or p-nitro-benzyl;

R$^2$ is

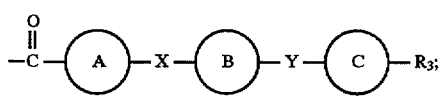

A, B, and C are independently selected from the following groups:

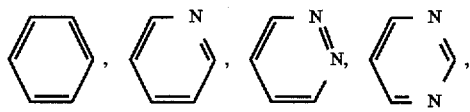

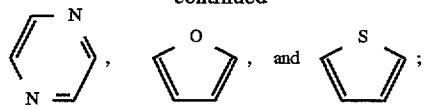

X and Y are independently a bond or —C≡C—;

R$^3$ is C$_1$–C$_{12}$ alkyl, C$_1$–C$_{12}$ alkoxy or —O—(CH$_2$)$_m$—[O—(CH$_2$)$_n$]$_p$—O—(C$_1$–C$_{12}$ alkyl);

m is 2, 3 or 4;

n is 2, 3 or 4; and p is 0 or 1;

with the proviso that A, B, and C cannot all be

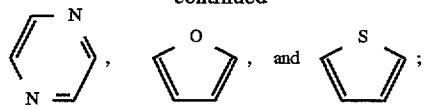

or a pharmaceutically acceptable salt thereof.

Also provided are pharmaceutical formulations, methods for inhibiting parasitic or fungal activity and methods of treating fungal or parasitic infections which employ the compounds of the invention.

The present invention also provides for the use of compounds of the invention for: inhibiting fungal activity, treating fungal infection, inhibiting parasitic activity, and treating or preventing the onset of Pneumocystis pneumonia in a host susceptible to Pneumocystis pneumonia.

DETAILED DESCRIPTION

As used herein, the term "C$_1$–C$_{12}$ alkyl" refers to a straight or branched alkyl chain having from one to twelve carbon atoms. Typical C$_1$–C$_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "C$_1$–C$_{12}$ alkyl" includes within its definition the terms "C$_1$–C$_6$ alkyl" and C$_1$–C$_4$ alkyl."

The term "halo" refers to chloro, fluoro, bromo or iodo.

The term "C$_1$–C$_{12}$ alkylthio" refers to a straight or branched alkyl chain having from one to twelve carbon atoms attached to a sulfur atom. Typical C$_1$–C$_{12}$ alkylthio groups include methylthio, ethylthio, propylthio, isopropylthio, butylthio, 3-methyl-heptylthio, octylthio, 5,5-dimethyl-hexylthio and the like.

The term "C$_1$–C$_{12}$ alkoxy" refers to a straight or branched alkyl chain having from one to twelve carbon atoms attached to an oxygen atom. Typical C$_1$–C$_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "C$_1$–C$_{12}$ alkyl" includes within its definition the terms "C$_1$–C$_6$ alkoxy" and C$_1$–C$_4$ alkoxy."

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, trimethylsilylethyl, (t-butyl)dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilylethyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy protecting groups.

The term "amino protecting group" as used in the specification refers to substituents of the amino group commonly employed to block or protect the amino functionality while reacting other functional groups on the compound. Examples of such amino protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino protecting groups. The species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are t-butoxycarbonyl (t-Boc), allyloxycarbonyl and benzyloxycarbonyl (Cbz). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;
$R^{x2}$ is hydrogen or hydroxy;
$R^0$ is hydroxy, —OP(O)(OH)$_2$ or a group of the formula:

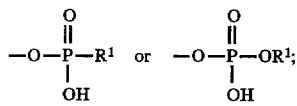

$R^1$ is methyl;
or a pharmaceutically acceptable salt thereof.

Of these compounds, more preferred are those compounds of formula I where:
$R^{x1}$ is hydrogen or hydroxy;
$R^{x2}$ is hydrogen or hydroxy;
$R^0$ is hydroxy;
$R^3$ is $C_1$-$C_{12}$ alkoxy or —O—(CH$_2$)$_2$—O—($C_1$-$C_{12}$ alkyl);
or a pharmaceutically acceptable salt thereof.

Of these compounds, further preferred are those compounds of formula I where:
$R^{x1}$ is hydroxy;
$R^{x2}$ is hydroxy;
X and Y are a bond;
$R^3$ is $C_1$-$C_8$ alkoxy;
or a pharmaceutically acceptable salt thereof.

Of these compounds even more preferred are those compounds of formula 1 wherein:

A is 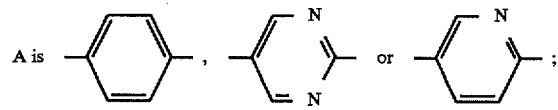

B is 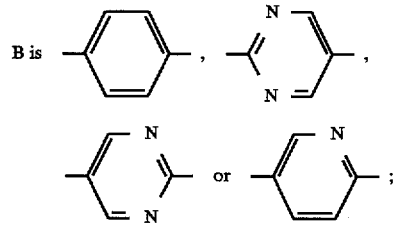

C is 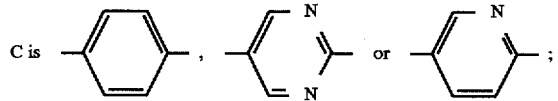

or a pharmaceutically acceptable salt thereof.

The compounds of formula I may be prepared according to Reaction Scheme I, as follows.

Reaction Scheme I

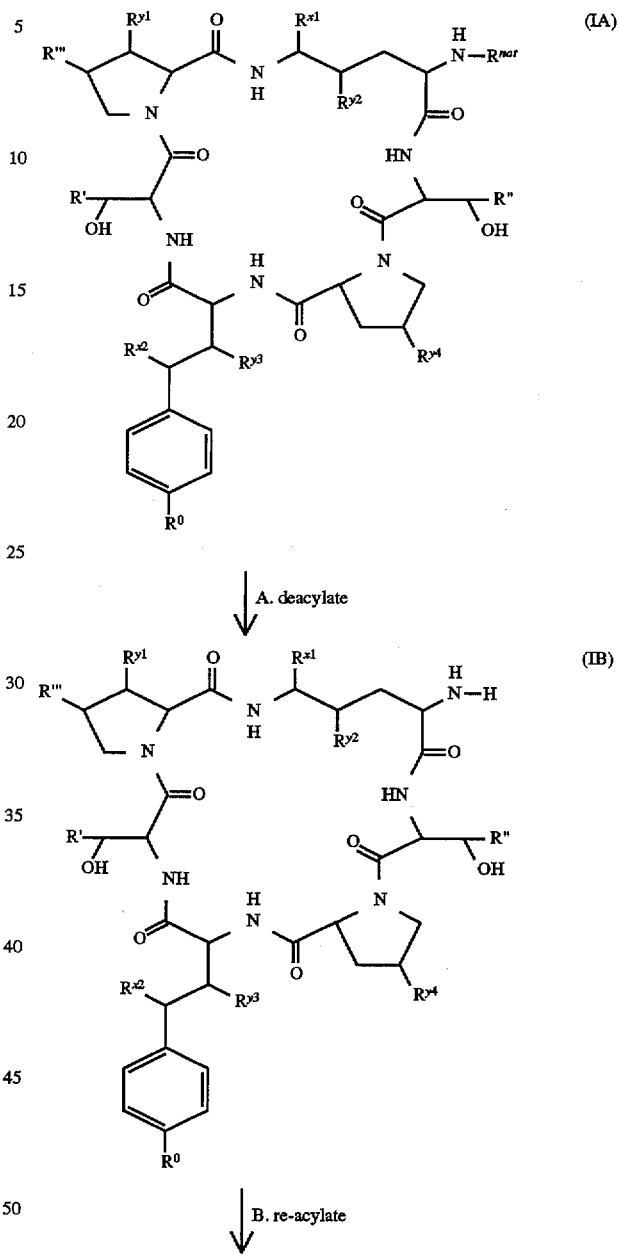

-continued
Reaction Scheme I

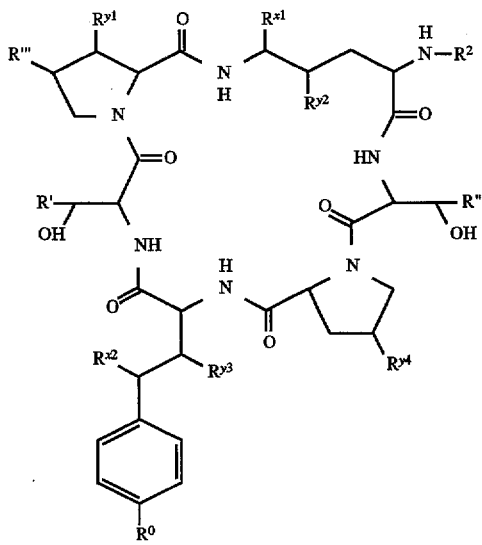

(I)

wherein:

$R^{nat}$ is a naturally occurring cyclic peptide sidechain; and R', R", R'", $R^{x1}$, $R^{x2}$, $R^{y1}$, $R^{y2}$, $R^{y3}$, $R^{y4}$, $R^0$ and $R^2$ are as defined above.

Reaction scheme I, above, is accomplished by carrying out reactions A and B, above. Once a reaction is complete, the intermediate compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization or precipitation or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), FR901379 (palmitoyl side chain) and the like. A preferred naturally occurring cyclic peptide is echinocandin B (a compound of formula IA where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is linoleoyl).

In Reaction IB, the amino nucleus of formula IB is then re-acylated using procedures known in the art to provide a compound of formula I where $R^0$ is hydroxy; $R^{x1}$ is hydroxy; and $R_2$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about −20° C. to about 25° C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazol-1-yloxytripyrrolidinophosphonium hexafluorophosphate (PyBOP) and the like.

In addition, the amino nucleus may be acylated with an activated ester of a carboxylic acid such as an ester of a carboxylic acid of the formula $R^2$—COOH and p-nitrophenyl, 2,4,5-trichlorophenyl, hydroxybenzotriazole hydrate (HOBT.$H_2O$), pentafluorophenol, N-hydroxysuccinimide and the like. Preferred acylating moieties are the active esters of the carboxylic acid $R^2$—COOH such as a benzotriazole ester. The reaction is typically carried out for one to sixty five hours at a temperature from about 0° C. to about 30° C. in an aprotic solvent. The reaction is generally complete after about twenty four to forty eight hours when carried out a temperature of from about 15° C. to about 30° C. Typical solvents for this reaction are tetrahydrofuran and dimethylformamide or a mixture of such solvents. The amino nucleus is generally employed in equimolar proportions relative to the activated ester or with a slight excess of the amino nucleus.

The compounds of formula I where $R^{x1}$ is hydroxy may be reacted with an appropriately substituted alcohol in the presence of an acid to provide a compound of formula I where $R^{x1}$ is —O—R, where R is $C_1$–$C_6$ alkyl, benzyl, —$(CH_2)_2Si(CH_3)_3$, —$CH_2CH$=$CH_2$, —$(CH_2)_a$COOH, —$(CH_2)_b NR^{z1}R^{z2}$, —$(CH_2)_c POR^{z3}R^{z4}$ or —$[(CH_2)_2O]_d$—$(C_1$–$C_6)$alkyl. The reaction is typically carried out in a polar aprotic solvent such as dioxane or dimethylsulfoxide at a temperature of from about 0° C. to about 35° C., preferably at about room temperature. Solvent choice is not critical so long as the solvent employed is inert to the ongoing reaction and the reactants are sufficiently solubilized to effect the desired reaction. Preferred acids include p-toluenesulfonic acid, hydrochloric acid and camphorsulfonic acid.

The compounds of formula I where $R^{x1}$ is —$(CH_2)_b NR^{z1}R^{z2}$ where $R^{z1}$ and $R^{z2}$ are hydrogen may be prepared via a protected compound wherein $R^{x1}$ is —$(CH_2)_b$NHR$^a$ where $R^a$ is an amino protecting group. The resultant protected compound is then deprotected according to procedures known in the art.

The compounds of formula I where $R^{x1}$ is —$CH_2CHOHCH_2OH$ may be prepared by hydroxylating a compound of formula I where $R^{x1}$ is —$CH_2CH$=$CH_2$ with osmium tetroxide in the presence of a catalyst at a temperature in the range of from about 0° C. to about 40° C. for about one to twenty four hours in a organic/aqueous solvent mixture, for example dioxane/water. Suitable catalysts include N-methylmorpholine N-oxide (NMO) and the like. Typical solvents suitable for use in this reaction include dimethylformamide, tetrahydrofuran, acetone and dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about eighteen to twenty four hours.

The compounds of formula I where $R^0$ is hydroxy may be phosphorylated by reaction with an appropriately substituted alkyl or phenyl phosphate to provide a compound of formula I where $R^0$ is —O—P(O)OH—$R^1$ where $R^1$ is $C_1$-$C_6$ alkoxy or phenoxy, or by reaction with an appropriately substituted alkyl or phenyl phosphonic acid to provide a compound of formula I where $R^0$ is —O—P(O)OH—$R^1$ where $R^1$ is $C_1$-$C_6$ alkyl, or an appropriately substituted phenyl or benzyl moiety, to provide a compound of formula I where $R^0$ is a group of the formula —OP(O)OH—$R^1$. The phosphonic acid is typically used in an activated form, for example as a phosphonic halide, preferably a phosphonic chloride. The reaction is carried out in the presence of a base such as lithium trimethylsilanolate (LiOTMS), lithium bis (trimethylsilyl)amide (LHMDS), pyridine and the like. The reaction is typically carried out for up to one hour at a temperature from about –30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups is typically carried out at lower temperatures, for example from about –30° C. to about –15° C.

Alternatively, the aminal hydroxy moieties on the compound of formula I are optionally protected with an hydroxy protecting group using procedures known in the art. For example, the reaction is typically carried out by combining the compound of formula I with a suitable hydroxy protecting group in the presence of a catalyst at a temperature in the range of from about 0° C. to about 40° C. for about one to five hours in a mutually inert solvent. The hydroxy protecting group is generally employed in an amount ranging from about equimolar proportions to about a 100 molar excess relative to the compound of formula I, preferably in a large molar excess. Suitable catalysts include strong acids such as p-toluenesulfonic acid, camphorsulfonic acid (CSA), hydrochloric acid, sulfuric acid, trifluoroacetic acid and the like. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about two to four hours. The protected compound of formula I is then phosphorylated as described above. The hydroxy protecting group(s) are then removed according to procedures known in the art to provide a phosphorylated compound of formula I. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The dideoxy compounds of formula I are prepared by removing the benzylic and aminal hydroxy groups ($R^{x2}$ and $R^{x1}$, respectively). The hydroxy groups may be removed by subjecting a non-dideoxy compound of formula I (where $R_2$ is hydrogen or acyl) to a strong acid and a reducing agent at a temperature of between –5° C. and 70° C., in a suitable solvent. Typical strong acids include trichloroacetic acid, trifluoroacetic acid or boron trifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 80 mol per mol of substrate, and the reducing agent should be present in an amount of 2 to 80 mol per mol of substrate. This process affords selective removal of the aminal and benzylic hydroxy groups.

The cyclic peptides used to make the compounds of the present invention may be prepared by fermentation of known microorganisms. For example, the cyclic peptide of formula IB where R', R" and R'" are methyl, $R^{x1}$, $R^{x2}$, $R^{y1}$, $R^{y2}$, $R^{y3}$, $R^{y4}$ and $R^0$ are each hydroxy (cyclic nucleus corresponding to A-30912A) may be prepared using the procedure detailed in Abbott et al., U.S. Pat. No. 4,293,482, which is herein incorporated by reference. The cyclic peptide of formula IB where R', R" and R'" are methyl, $R^{x1}$ is hydroxy, $R^{x2}$ is hydrogen, $R^{y1}$, $R^{y2}$, $R^{y3}$, $R^{y4}$ and $R^0$ are each hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is —$CH_2C(O)NH_2$, R" is methyl, R'" is hydrogen, $R^{x1}$, $R^{x2}$, $R^{y1}$, $R^{y2}$, $R^{y3}$, $R^{y4}$ and $R^0$ are each hydroxy may be prepared by deacylating the cyclic peptide prepared using the procedure detailed in Chen et al., U.S. Pat. No. 5,198,421, which is herein incorporated by reference.

The $R^2$—COOH precursor acids may be obtained commercially or prepared according to procedures known in the art. For example, an appropriately substituted aryl boronic acid or biaryl boronic acid reactant may be reacted with a haloaryl carboxylic acid reactant in the presence of a catalyst such as tetrakis(triphenylphosphine)palladium and an inorganic base such as potassium carbonate in a mutual inert organic solvent such as toluene at a temperature of from about 20° C. to the reflux temperature of the reaction mixture to provide the corresponding biaryl carboxylic acids and teraryl carboxylic acids used to prepare the compounds of formula I. The reaction is typically carried out with equimolar proportions of the boronic acid reactant and the aryl carboxylic acid reactant, or a slight molar excess of the aryl carboxylic acid reactant relative to the boronic acid reactant, and a 1–2 molar excess of the inorganic base. The reaction is generally complete after about four to about ten hours when carried out at reflux temperature in toluene.

The boronic acid reactant may be prepared by reacting an appropriately substituted haloaryl or halobiaryl reactant with two equivalents of triisopropyl borate in the presence of an alkyl lithium, for example sec-butyl lithium, in a mutual inert solvent such as tetrahydrofuran. The alkyl lithium is typically employed in a slight molar excess relative to the haloaryl or halobiaryl reactant. The alkyl lithium is typically combined with the solvent by dropwise addition at reduced temperatures (<–70° C.) and allowed to stir for approximately thirty minutes before the addition of the triisopropyl borate. The reaction is typically carried out initially at a temperature of from about –100° C. to about –50° C., preferably from about –75° C. to about –85° C. for thirty minutes to two hours and then warmed to room temperature and reacted for an additional one to three hours. The reaction is generally complete in several minutes to about four hours. When the reaction is substantially complete, the boronic acid moiety is formed by the addition of an acid. A preferred acid is a 1N hydrochloric acid solution.

The $R^2$—COOH precursor acids having an acetylene moiety may be prepared by reacting an appropriately substituted acetylene reactant with an appropriately substituted aryl or biaryl reactant of the formula

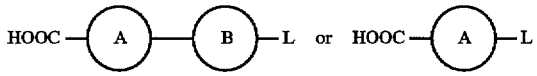

where L is a suitable leaving group such as bromo, iodo, methanesulfonate, toluenesulfonate, trifluoromethanesulfonate and the like, in the presence of a catalyst and preferably in the presence of an acid scavenger in a mutual inert solvent such as acetonitrile. Examples of acid scavengers include triethylamine and pyridine, preferably triethylamine. A preferred catalyst is formed in situ from palladium (II) chloride, triphenylphosphine and copper (I) iodide. The reaction is typically carried out for thirty minutes to twenty one hours at a temperature from about room temperature to the reflux temperature of reaction mixture. The reaction is generally complete after about two to about six hours when carried out at reflux temperature.

Alternatively, a suitably substituted aryl reactant of the formula

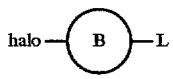

may be reacted with an appropriately substituted acetylene reactant as described above to provide, for example, a compound of the formula

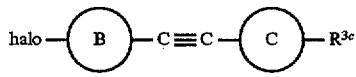

which can be coupled with an aryl boronic acid reactant as described above.

Compounds of the present invention wherein $R^{x1}$ is NHR or where R' is $CH_2CH_2NH_2$ can be prepared by procedures and schemes disclosed herein in combination with procedures well known in the art. For example such preparations are exemplifed by but not limited to the following publications: WO94/25048; WO94/25050; WO 96/08266; and WO 96/08507.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC" and "TLC", respectively. In addition, the absorption maxima listed for the IR spectra are only those of interest and not all of the maxima observed.

Preparation 1

6-Chloronicotinic acid, methyl ester

Hydrochloric acid (gas) was bubbled through a solution of 6.11 g (38.8 mmol) of 6-chloronicotinic acid in approximately 350 ml of methanol. The resultant reaction mixture was reacted for approximately two hours at reflux temperature, then cooled to room temperature and concentrated in vacuo to provide a white residue. This residue was redissolved in methylene chloride and the resultant solution was washed with a saturated sodium bicarbonate solution. The organic portion was dried over sodium sulfate, filtered and then reduced to dryness in vacuo to provide 7.28 g of a tan solid. This solid was crystallized from pentane, followed by recrystallization from hexane to provide the desired titled compound.

Preparation 2

A. 1-Bromo-4-pentoxy-benzene

To a solution containing 25.017 g (0.144 mol) of 4-bromo-phenol and 24.44 g (0.218 mol) of potassium t-butoxide in 500 ml of tetrahydrofuran, was added 27 ml (0.218 mol) of 1-bromopentane, via syringe. The resultant reaction mixture was reacted overnight at reflux temperature. When the reaction was substantially complete, as indicated by TLC, the reaction mixture was filtered. The filtrate was concentrated in vacuo to provide a residue which was redissolved in diethyl ether and the resultant solution was washed sequentially with water and 1M sodium hydroxide. The organic portion was dried over sodium sulfate, filtered and then concentrated in vacuo to provide 3.062 g of an oil that was used without further purification.

Yield: 87%.

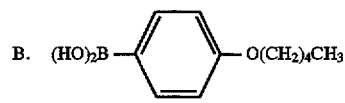

To a cold (−76° C.) solution of 6.0 g (24.6 mmol) of the subtitled compound of Preparation 2A in 500 ml of tetrahydrofuran, was added 21.5 ml of a 1.6M solution of sec-butyllithium (34.4 mmol) in hexane, via syringe. After approximately twenty minutes, 12 ml (52 mmol) of triisopropyl borate was added, via syringe. The resultant reaction mixture was warmed to room temperature followed by the addition of 60 ml of a 1N hydrochloric acid solution. After approximately ten minutes, the reaction mixture was concentrated in vacuo to provide a pale yellow solid. This solid was recrystallized from diethyl ether, followed by recrystallization from hexanes to provide a white solid.

Yield: 2.95 g (57%).

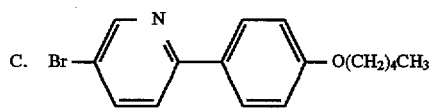

To a solution of 1.44 g (6.92 mmol) of a subtitled compound of Preparation 2B in 50 ml of toluene and 20 ml of methanol under nitrogen, was added 15.5 ml (31.1 mmol) a 2M sol. of sodium carbonate which resulted in the formation of a white precipitate. To the resultant mixture, was added 800 mg (0.69 mmol) of palladium tetrakis (triphenylphosphine), followed by 1.64 g (6.92 mmol) of 2,5-dibromopyridine. The resultant reaction mixture was reacted for approximately three hours, forty-five minutes at reflux temperature. When the reaction was substantially complete, as indicated by TLC, the mixture was cooled to room temperature and allowed to stir overnight. The reaction mixture was placed in a separatory funnel and combined with diethyl ether and water. The resultant layers were separated and the organic layer was dried over sodium sulfate, filtered and then concentrated in vacuo to provide a residue. This residue was redissolved in pentane and filtered to provide 0.95 g of the desired compound. The filtrate was recrystallized to provide an additional 1.4 g of the desired compound. These solids were combined and used without further purification.

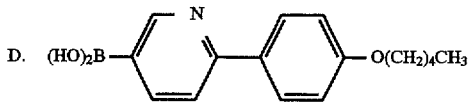

The desired subtitled compound was prepared substantially in accordance with the procedure detailed in Preparation 2B, using 15.8 ml of a 1.3M sec-butyllithium solution (20.54 mmol), 7 ml (30.33 mmol) of triisopropyl borate, 125 ml of a 1N hydrochloric acid solution and 450 ml of anhydrous tetrahydrofuran.

Yield: 4.0 g of an orange solid.

Preparation 3

A. 2-Heptoxy-5-bromo-pyridine

A solution of 20.4 ml (0.048 mol) of heptanol in 50 ml of toluene was slowly added to a warm (50° C.) slurry of 5.76 g of 60% sodium hydride (0.144 mol) in 400 ml of dimethylformamide, under nitrogen, which resulted in the evolution of hydrogen gas. After stirring the resultant mixture at 80° C. for approximately two hours, 30 g (0.126 mol) of 2,5-dibromopyridine was slowly added. The resultant reaction mixture was refluxed overnight. The new mixture was poured into water. The desired compound was extracted from the resultant mixture using diethyl ether and the organic portions were then washed with water, dried over magnesium sulfate, filtered and concentrated in vacuo to provide 35 g of an oil. Purification with column chromatography using silica gel (eluent of 10% ethyl acetate in hexane) to provide a clear oil.

Yield: 20.7 g (60%).

HPLC: $C_{18}$ reverse-phase column; eluent of 20% water in acetonitrile; λ=254 nm; 2 ml/min; $R_T$=6.03 min;

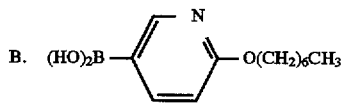

The desired subtitled compound was prepared substantially in accordance with the procedure detailed in Preparation 2B, using 2.72 g (10 mmol) of the subtitled compound of Preparation 3A, 10 ml (16 mmol) of a 1.6M solution of sec-butyllithium in hexane, 5.5 ml (24 mmol) of triisopropyl borate, 50 ml of a 1N hydrochloric acid solution and 60 ml of diethyl ether.

Yield: 1.98 g of a white solid (83%).

HPLC: $C_{18}$ reverse-phase column; eluent of 20% water in acetonitrile; λ=254 nm; 2 ml/min; $R_T$=2.53 min;

Preparation 4

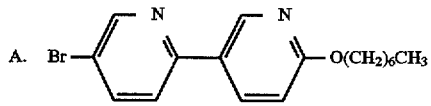

A solution of 230 mg (0.25 mmol) of tris (dibenzylideneacetone)dipalladium and 520 mg (2 mmol) of triphenylphosphine in 5 ml of toluene was added to a solution of 1.11 g (4.7 mmol) of 2,5-dibromopyridine, 1.13 g (4.7 mmol) of the subtitled compound of Preparation 3B and 1.15 g (10.85 mmol) of sodium carbonate in 40 ml of toluene, 30 ml of methanol and 13 ml of water, under nitrogen. The resultant reaction mixture was reacted for approximately two hours at reflux temperature. When the reaction was substantially complete, as indicated by HPLC, the reaction mixture was concentrated in vacuo to provide a residue. This residue was dissolved in diethyl ether and then washed sequentially with a 1N hydrochloric acid solution and a 2N sodium hydroxide solution, dried over sodium sulfate, filtered and then reduced to dryness in vacuo to provide a solid. This solid was redissolved in pentane and the resultant mixture was filtered. The filtrate was cooled resulting in the formation of a white solid which was collected by filtration.

Yield: 0.4865 g (30%).

m.p. 47°–49° C.

MS(FD): 348 (M–1).

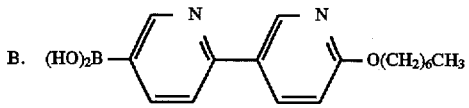

The desired subtitled compound was prepared substantially in accordance with the procedure detailed in Preparation 2B, using 0.48 g (1.38 mmol) of the subtitled compound of Preparation 4A, 1.4 ml of a 1.6M solution of sec-butyllithium in hexane (2.2 mmol), 0.76 ml (3.3 mmol) of triisopropyl borate, an excess of a 1N hydrochloric acid solution and 50 ml of diethyl ether.

Yield: 0.439 g.

Preparation 5

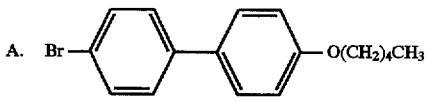

A solution containing 50 g (200 mmol) of 4-bromophenol, 33.5 g (298 mmol) of potassium t-butoxide and 40 ml (298 mmol) of 1-iodopentane in 1000 ml of tetrahydrofuran was reacted at reflux temperature for approximately twenty four hours. When the reaction was substantially complete, as indicated by TLC the reaction was filtered. The resultant filtrate was concentrated in vacuo to provide a purple solid. This solid was redissolved in a water/diethyl ether mixture to provide a yellow solution. This solution was washed sequentially with 200 ml of water (twice), 100 ml of 2N sodium hydroxide (twice) and 200 ml of brine (twice), dried over sodium sulfate and then concentrated in vacuo to provide a yellow powder. This solid was recrystallized from hot hexanes to provide a white powder.

Yield: 45.8 mg (72%).

B. 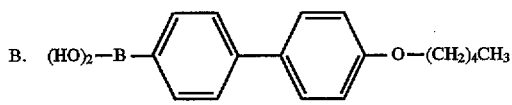

To a cold (−78° C.) solution of 10.0 mg (42.9 mmol) of 29 g (90.8 mmol) of the compound of Preparation 5A, was added 91 ml of sec-butyllithium in 1000 ml of tetrahydrofuran (118 mmol), dropwise. To the resulting mixture was added 41.9 ml (181.7 mmol) of triisopropyl borate, dropwise. The resultant reaction mixture was stirred for approximately thirty minutes and then warmed to room temperature and allowed to react for approximately two hours. The reaction was then quenched by the addition of 1N hydrochloric acid. The resultant mixture was concentrated in vacuo to provide a residue. This residue was redissolved in diethyl ether, filtered and reduced to dryness to provide the desired subtitled compound.

Preparation 6

A. 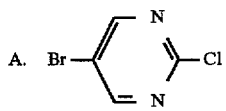

A mixture of 8.14 g (46.5 mmol) of 2-hydroxy-5-bromopyrimidine in 25 ml of phosphorus oxychloride (268 mmol) was refluxed for 1.5 hours. After allowing the reaction mixture to cool to room temperature, the excess phosphorus oxychloride was removed by distillation. Ice water was added to the residue, followed by sodium hydroxide until pH 7. The aqueous layer was extracted three times with ethyl acetate. The organic layer was dried over sodium sulfate, filtered and then concentrated in vacuo to provide 7.16 g of the desired compound.

Yield: 80%.

B. 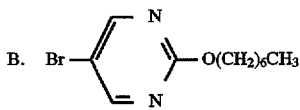

To a warm (93°) suspension of 2.11 g (52.8 mmol) of 60% sodium hydride in 100 ml of toluene and 100 ml of dimethylformamide, was added 7.3 ml (51.6 mmol) of heptanol, dropwise, which resulted in the evolution of hydrogen gas. After stirring the resultant mixture at 115° C. for approximately two hours, a solution of 4.94 g (25.6 mmol) of the subtitled compound of Preparation 6A was added. After reacting overnight at reflux temperature, the reaction mixture was cooled to room temperature and poured over ice water. The desired compound was extracted from the resultant mixture using diethyl ether. The resultant mixture was washed three times with water, dried over sodium sulfate, filtered and then concentrated in vacuo to provide a dark brown oil which was purified using column chromatography (gradient eluent of 5–10% ethyl acetate in hexane) to provide 2.65 g of the desired compound.

Yield: 38%.

C. 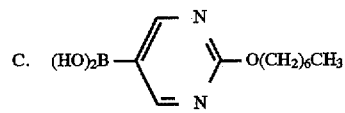

The desired subtitled compound was prepared substantially in accordance with the procedure detailed in Preparation 2B, using 2.77 g (10.1 mmol) of the subtitled compound of Preparation 6B, 12 ml of a 1.3M solution of sec-butyllithium in hexane, 400 g or 21.3 mmol (15.6 mmol) of triisopropyl borate, 16 ml of a 1N hydrochloric acid solution. The resultant layers were separated and the organic layer was concentrated in vacuo to provide 2.83 g of a crude material which was used without further purification.

Preparation 7

A. 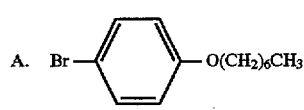

The desired subtitled compound was prepared substantially in accordance with the procedure detailed in Preparation 2A, using 51 g (0.29 moles) of 4-bromo-phenol, 49.4 g (0.44 moles) of 1-bromoheptane in 800 ml of tetrahydrofuran to provide 77 g of an oil which was used without further purification.

B. 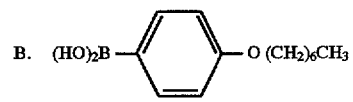

The desired subtitled compound was prepared substantially in accordance with the procedure detailed in Preparation 2B, using 2.72 g (10 mmol) of the subtitled compound of Preparation 7A, 10 ml (16 mmol) of a 1.6M solution of sec-butyllithium in hexane, 5.5 ml (24 mmol) of triisopropyl borate, 50 ml of a 1N hydrochloric acid solution and 60 ml of diethyl ether.

Yield: 1.98 g of a white solid (83%).

C. 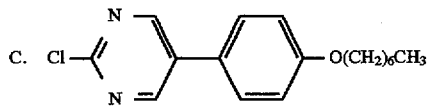

The desired subtitled compound was prepared substantially in accordance with the procedure detailed in Preparation 2C, using 1.22 g (5.16 mmol) of the subtitled compound of Preparation 7B, 1.0 g (5.16 mmol) of the subtitled compound of Preparation 6A, 598.3 mg (0.516 mmol) of palladium tetrakis (triphenylphosphine), 11.6 ml of a 2M sodium carbonate solution (23 mmol), 25 ml of toluene and 10 ml of methanol.

Yield: 1.4520 g (92%).

D. 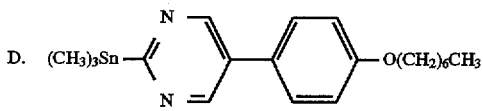

To a solution of 613.0 mg (2.01 mmol) of the subtitled compound of Preparation 7C and 119.3 mg (0.1 mmol) of palladium tetrakis(triphenylphosphine) in 10 ml of dioxane, was added 760 mg (2.32 mmol) of hexamethylditin under nitrogen. The resultant reaction mixture was reacted overnight at reflux temperature. After cooling to room temperature, the reaction mixture was concentrated in vacuo to provide a residue. This residue was redissolved in 20 ml of diethyl ether, combined with a saturated potassium fluoride solution and stirred for approximately 3.5 hours. The resultant layers were separated and the organic layer was concentrated in vacuo to provide the desired subtitled compound which was used without further purification.

Preparation 8

5-Bromofuranoic acid, methyl ester

To a slurry of 15.00 g (0.0785 mol) of 5-bromofuranoic acid in 500 ml of methylene chloride, was added 12.73 g (0.0785 mol) of N,N-carbonyldiimidazole. After reacting at room temperature overnight, 6.4 ml (0.157 mol) of methanol was added and the resultant mixture was stirred for approximately one hour and then washed sequentially with a 0.5M sodium hydroxide solution (twice) and a 1M hydrochloric acid solution. The organic portion was dried over sodium sulfate, filtered and then concentrated in vacuo to provide a residue. This residue was slurried in pentane to provide a white solid.

Yield: 13.15 g (82%).

$^1$H NMR: δ 7.17 (d, 1H, CH); 6.45 (d, 1H, CH); 3.89 (5, 3H, CH$_3$).

Preparation 9

N-methanesulfonate benzotriazole

To a cold (5° C.) solution of 100 g (0.653 mol) of hydroxybenzotriazole (HOBT) in 750 ml of methylene chloride, was added 82.59 g (0.816 mol) of triethylamine while maintaining the temperature at 5°–10° C. followed by the addition of 82.28 g (0.718 mol) of methanesulfonyl chloride while maintaining the temperature at 4°–10° C. The resultant reaction mixture was reacted for approximately one hour at 4° C. When the reaction was substantially complete, as indicated by TLC, the reaction mixture was transferred to a separatory funnel and washed sequentially with water (three times) and a saturated sodium chloride solution, dried over sodium sulfate, filtered and concentrated in vacuo to provide a solid. This solid was combined with a small amount of diethyl ether and the resultant mixture was filtered and dried in vacuo to provide a white solid.

Yield: 126.2 g (91%).

Preparation 10

A. 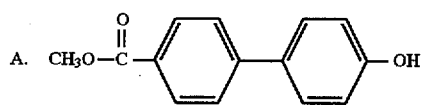

A solution of 50 g (0.26 mol) 4-cyano-4'-hydroxybiphenyl and an excess of 50% sodium hydroxide in 2000 ml of ethanol was refluxed for three hours. After cooling to room temperature, the reaction mixture was acidified with concentrated hydrochloric acid which resulted in the formation of a solid which was collected by filtration. The solid was suspended in 20 ml of concentrated hydrochloric acid in methanol and refluxed overnight. After cooling to room temperature, water was added to the solution which resulted in the formation of a solid. This solid was collected by filtration and dried in vacuo overnight at 60° C.

Yield: 52.6 g (81%).

B. 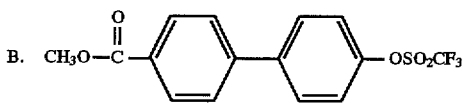

To a cold (0° C.) solution of 16.2 g (0.07 mol) of 4-hydroxy-4'-carboxymethyl biphenyl in pyridine, was added 50 g (0.177 mol) of trifluoromethylsulfonic acid anhydride, dropwise. The resultant reaction mixture was stirred for 1 hour, and then was concentrated in vacuo to provide a residue. This residue was redissolved in diethyl ether, washed with a 1N hydrochloric acid solution, dried over sodium sulfate, filtered, and then concentrated in vacuo to provide an oil. This oil solidified when slurried in pentane and the solid was collected by filtration.

Yield: 40.1 g (80%).

m.p. 57°–58° C.

MS(FD): 360.

Elemental Analysis: Calcd: C, 50.00; H, 3.05; Found: C, 50.30; H, 3.11.

Preparation 11

A. 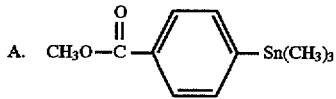

To a solution of 6.05 g (23.1 mmol) of methyl 4-iodobenzoate and 1.6 g (1.38 mmol) of palladium tetrakis(triphenyl)phosphine in 250 ml of dioxane, was added 8.81 g (27 mmol) of hexamethylditin, under nitrogen. The resultant reaction mixture was reacted for four hours at reflux temperature. After cooling to room temperature, the reaction mixture was concentrated in vacuo to provide a residue. This residue was redissolved in diethyl ether and a saturated potassium fluoride solution and stirred overnight at room temperature. The resultant layers were separated and the organic layer was concentrated in vacuo to provide 7.1 g of a solid which was used without further purification.

$^1$H NMR: (CDCl$_3$) δ 7.95 (d, 2H, ArH); 7.59 (d, 2H, ArH); 3.95 (s, 3H, CH$_3$); 0.36 (s, 6H, CH$_3$).

B. 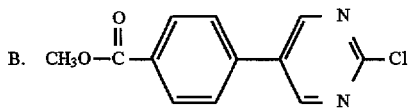

A solution containing 4.0 g (13.3 mmol) of the subtitled compound of Preparation 11A, 2.5 g (13.3 mmol) of the subtitled compound of Preparation 6A, 192.7 mg (1.34 mmol) of copper(II) bromide, and 769.7 mg (0.66 mmol) of palladium tetrakis(triphenylphosphine) in 80 ml of dimethylformamide, under nitrogen, was refluxed for 2.5 hours. After cooling to room temperature, the reaction mixture was concentrated in vacuo to provide a residue. This residue was redissolved in a mixture of diethyl ether and a saturated potassium fluoride solution and then stirred at room temperatue for approximately forty eight hours. The resultant layers were separated and the organic layer was concentrated in vacuo to provide 1.88 g of crude material which was purified using column chromatography (eluent of 1% ethyl acetate in methylene chloride).

Yield: 0.47 g (14%).

MS(FAB) for $C_{56}H_{72}N_9O_{17}$ (M+1): Calcd: 1142.5046 Found: 1142.5085.

Preparation 12

A. 2-Ethoxymethyl-1-propenoic acid, ethyl ester

To a cold (0° C.) gel-like mixture of 25 ml (0.162 mmol) of ethoxypropanoic acid, ethyl ester and 40 ml (0.495 mol) of formic acid, ethyl ester, was added 35 ml (0.37 mol) of dimethylsulfate, dropwise. The resultant reaction mixture was warmed to room temperature and then heated to 60° C. and allowed to react overnight. After adding more dimethylsulfate (6 ml), the reaction mixture was heated to 60° C. and stirred for five hours. After cooling to room temperature, an aqueous solution of 2M sodium carbonate was added to the reaction mixture to bring the mixture to pH 12. The resultant layers were separated and the organic layer was dried over sodium sulfate, filtered and concentrated in vacuo to provide the subtitled compound.

Yield: 8.56 g (28%).

B. 2-Oxo-5-ethoxycarbonyl-1,3,6-trihydropyrimidine

To a mixture of 1.0044 g (5.34 mmol) of the subtitled compound of Preparation 12A in ethanol, was added 321.2 mg (5.35 mmol) of urea, followed by approximately 0.52 μl of concentrated hydrochloric acid. The resultant reaction mixture was refluxed for approximately 8.25 hours and then stirred overnight at room temperature. The reaction mixture was concentrated in vacuo to provide a white solid. This solid was recystallized in ethanol to provide 321 mg of the desired compound.

m.p. 167°–172° C.

MS(FD): 171.

C. 2-oxo-5-ethoxycarbonyl-3-monohydropyrimidine hydrobromide

A solution of 3.31 g (20.7 mmol) of bromine in 14 ml of glacial acetic acid was added to a mixture of 3.52 g (20.7 mmol) of the subtitled compound of Preparation 12B in 71 ml of glacial acetic acid. The resultant reaction mixture was reacted at reflux temperature. The resultant crude material was used without further purification.

Yield: 3.9773 g (77%).

m.p. 198°–200° C. (decomp.).

D. 2-Chloro-5-ethoxycarbonyl-pyrimidine

To 3.659 g (14.7 mmol) of the subtitled compound of Preparation 12C, was added 20.5 ml (220 mmol) of phosphorus oxychloride, followed by 2 ml (26.6 mmol) of dimethylphenylamine. The resultant reaction mixture was slowly added to cold water. The resultant layers were separated and the aqueous layer was neutralized by the addition of a 5N sodium hydroxide solution and then the desired compound was extracted using ethyl acetate. The extracts were combined and then concentrated in vacuo to provide a residue. This residue was slurried in hot hexanes and the resultant mixture was cooled to room temperature and filtered. The filtrate was concentrated in vacuo to provide a yellow solid.

Yield: 0.9096 g (33%).

EXAMPLE 1

A. 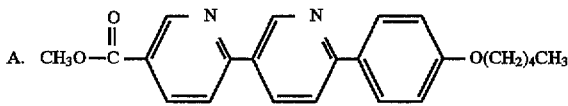

The desired subtitled compound was prepared substantially in accordance with the procedure detailed in Preparation 2C, using 1.99 g (6.98 mmol) of the subtitled compound of Preparation 2D, 1.25 g (7.28 mmol) of the titled compound of Preparation 1, 0.811 g (0.73 mmol) of palladium tetrakis (triphenylphosphine), 15.8 ml (31.6 mmol) of a 2N sodium carbonate solution, 50 ml of toluene and 20 ml of methanol.

Yield: 1.3381 g (51%).

B. 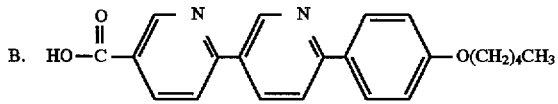

A mixture of 1.336 g (3.55 mmol) of the subtitled compound of Example 1A and 9.3 ml of a 2N sodium hydroxide solution (18.6 mmol) in 250 ml of dioxane was refluxed overnight. After cooling the reaction mixture to room temperature, 18.6 ml of a 1N hydrochloric acid solution was added, which resulted in the formation of a precipitate. This precipitate was isolated by filtration to provide 1.044 g of material that was used without further purification.

Yield: 81%.

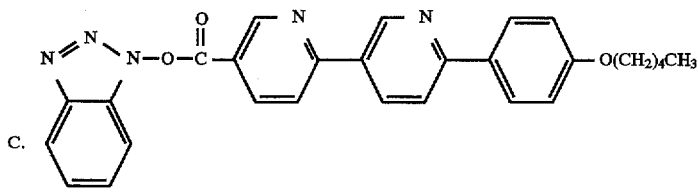

To a mixture of 1.02 g (2.81 mmol) of the subtitled compound of Example 1B in 95 ml of dimethylformamide, was added 630.6 mg (2.96 mmol) of the titled compound of Preparation 9, followed by 0.422 ml (3.035 mmol) of triethylamine. After reacting at room temperature for approximately 2.5 hours, the reaction mixture was concentrated in vacuo to provide a black residue. This residue was redissolved in methylene chloride, washed with water, filtered, dried over sodium sulfate, filtered and then concentrated in vacuo to provide 1.34 g of solid which was used without further purification.

D. Preparation of the compound of formula I where R' R" and R'" are each methyl and $R^{x1}$, $R^{x2}$, $R^{y1}$, $R^{y2}$, $R^{y3}$, $R^{y4}$ and $R^o$ are each hydroxy and $R^2$ is

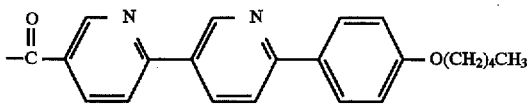

To a solution of 1.34 g (2.79 mmol) of the subtitled compound of Example 1C in dimethylformamide, was added 2.13 g (2.61 mmol) of the A-30912A nucleus (compound of formula 1B where R', R" and R'" are each methyl, $R^{x1}$ $R^{x2}$, $R^{y1}$, $R^{y2}$, $R^{y3}$, $R^{y4}$ and $R^o$ are each hydroxy). After reacting at room temperature overnight, under nitrogen, the reaction mixture was filtered. The resultant filtrate was concentrated in vacuo to provide a residue which was slurried in diethyl ether, filtered and then slurried in methylene chloride and filtered to provide a gold powder. This powder was redissolved in methanol and then purified using HPLC (eluent of 35% acetonitrile, 55% water and 10% of a 1% aqueous trifluoroacetic acid solution). The fractions containing the desired compound were combined and concentrated in vacuo to provide 1.20 g (39%) of the desired compound.

MS(FAB) for $C_{56}H_{72}N_9O_{17}$ (M+H): Calcd: 1142.5046; Found: 1142.5085.

EXAMPLE 2

A. 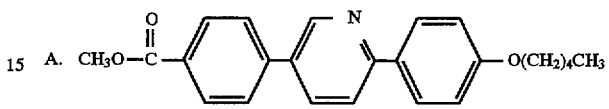

The desired subtitled compound was prepared substantially in accordance with the procedure detailed in Preparation 2C, using 2.00 g (7.01 mmol) of the subtitled compound of Preparation 2D, 2.02 g (7.71 mmol) of methyl-4-iodobenzoate, 830 mg (0.70 mmol) of palladium tetrakis (triphenylphosphine), 16 ml (31.5 mmol) of 2M sodium carbonate, 50 ml of toluene and 20 ml of methanol to provide an off-white powder which was used without purification.

Yield: 2.28 g (90%).

B. 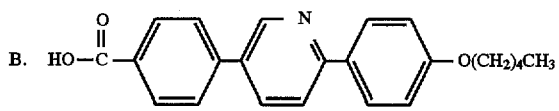

The desired subtitled compound was prepared substantially in accordance with the procedure detailed in Example 1B, using 2.28 g (6.3 mmol) of the subtitled compound of Example 2A, 16.6 ml of a 2N sodium hydroxide solution (33.2 mmol), 500 ml of dioxane and 33.2 ml of a 1N hydrochloric acid solution.

Yield: 1.55 g (71%).

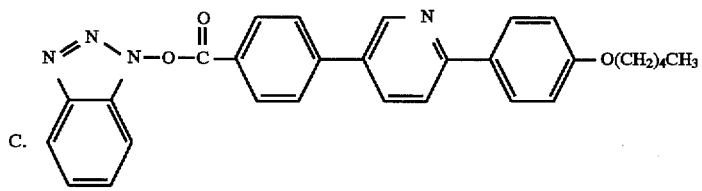

The desired subtitled compound was prepared substantially in accordance with the procedure detailed in Example 1C, using 1.55 g (4.46 mmol) of the subtitled compound of Example 2B, 1.02 g (4.78 mmol) of the titled compound of Preparation 9, 0.67 ml (4.82 mmol) of triethylamine and 125 ml of dimethylformamide to provide 0.320 g of a tan powder.

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R_2$ is

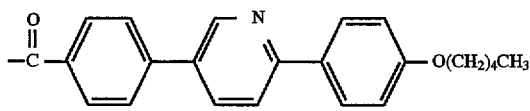

The desired subtitled compound was prepared substantially in accordance with the procedure detailed in Example 1D, using 0.320 g (0.668 mmol) of the subtitled compound of Example 2C, 486.4 mg (0.609 mmol) of the A-30912A nucleus in dimethylformamide.

Yield: 0.2832 (41%)

MS (FAB) for $C_{57}H_{72}N_8O_{17}Li$: Calcd: 1147.5205; Found: 1147.5175.

EXAMPLE 3

A. 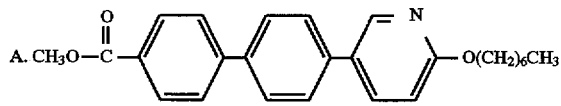

A solution of 230 mg (0.25 mmol) of tris(dibenzylidene acetone) dipalladium (0) ($Pd_2dba_3$) and 520 mg (2 mmol) of triphenylphosphine in 10 ml of toluene was added to a solution containing 1.4 g (3.9 mmol) of 1-methoxycarbonyl-4-(4'-trifluorosulfonate)biphenyl, 1.13 g (4.7 mmol) of the subtitled compound of Preparation 3B, 1.15 g (10.85 mmol) of sodium carbonate in 30 ml of toluene, 20 ml of methanol and 13 ml of water. The resultant reaction mixture was refluxed overnight, cooled and the resultant layers were separated. The organic layer was concentrated in vacuo to provide a residue. This residue was slurried in methanol and then filtered to provide 0.797 g of a solid which was determined to be 98% pure using HPLC (eluent of 90% acetonitrile in water; λ=254; 3 ml/min.; $R_T$=3.76 min.).

Yield: 51%.

B. 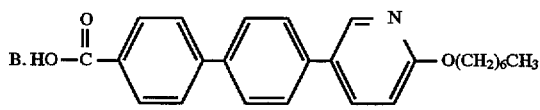

The desired subtitled compound was prepared substantially in accordance with the procedure detailed in Example 1B, using 0.797 g (1.9 mmol) of the subtitled compound of Example 3A, 5 ml of a 2N sodium hydroxide solution (10 mmol), 200 ml of dioxane and 10 ml of a 1N hydrochloric acid solution.

Yield: 518 mg (70%).

C. 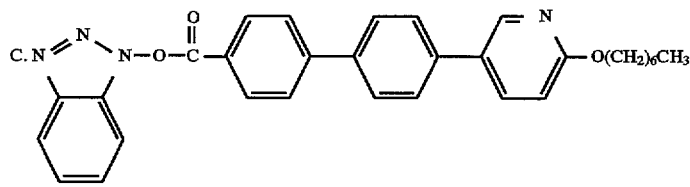

The desired subtitled compound was prepared substantially in accordance with the procedure detailed in Example 1C, using 0.512 g (1.33 mmol) of the subtitled compound of Example 3B, 298 mg (1.4 mmol) of the titled compound of Preparation 9, 0.195 ml (1.4 mmol) of triethylamine and 50 ml of dimethylformamide to provide 145 mg of solid which was determined to be 95% pure using HPLC (eluent of 90 acetonitrile in water, 3 ml/min., λ=280 nm, $R_T$=3.88 min.).

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R_2$ is

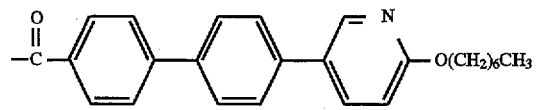

The desired subtitled compound was prepared substantially in accordance with the procedure detailed in Example 1D, using 225 mg (0.445 mmol) of the subtitled compound of Example 3C, 355 mg (0.445 mmol) of the A-30912A nucleus in dimethylformamide to provide 314 mg of a white solid which was determined to be 99.6% pure using HPLC (eluent of 55% acetonitrile in water containing 0.5% monoammonium phosphoric acid, λ=230 nm, 2 ml/min., $R_T$=4.35 min.).

MS (FAB) for $C_{59}H_{77}N_8O_{17}$: Calcd: 1169.5407; Found: 1169.5391.

EXAMPLE 4

A. 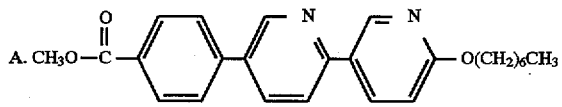

The desired subtitled compound was prepared substantially in accordance with the procedure detailed in Example 3A, using 47 mg (0.051 mmol) of $Pd_2dba_3$, 106 mg (0.41 mmol) of triphenylphosphine, 253 mg (0.97 mmol) of methyl-4-iodobenzoate, 303 mg (0.97 mmol) of the subtitled compound of Preparation 4B, 0.46 g (4.4 mmol) of sodium carbonate in 8 ml of toluene, 6 ml of methanol and 2.6 ml of water to provide 11 mg of a solid which was determined to be 90% pure using HPLC (eluent of 90% acetonitrile in water, 2 ml/min., λ=280 nm, $R_T$=5.15 min.).

B. 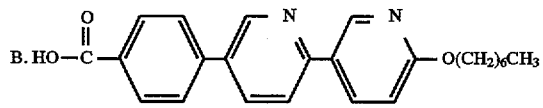

The desired subtitled compound was prepared substantially in accordance with the procedure detailed in Example 1B, using 0.458 g (1.13 mmol) of the subtitled compound of Example 4A, 5 ml of a 2N sodium hydroxide solution (10 mmol), 60 ml of dioxane and 10 ml of a 1N hydrochloric acid solution to provide 0.51 g of material that was used without further purification.

subtitled compound of Preparation 4B, 1.3 g (12.2 mmol) of sodium carbonate in 22 ml of toluene, 16 ml of methanol and 7 ml of water to provide 206.9 mg of a solid which was determined to be 96% pure using HPLC (eluent of 90% acetonitrile in water, 3 ml/min., λ=280 nm, $R_T$=3.13 min.).

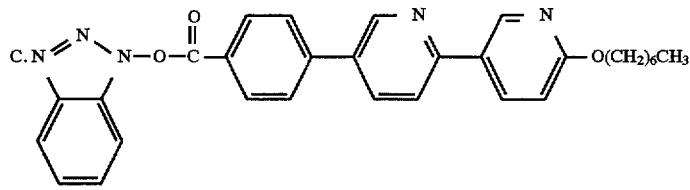

The desired subtitled compound was prepared substantially in accordance with the procedure detailed in Example 1C, using 0.51 g of the subtitled compound of Example 4B, 298 mg (1.4 mmol) of the titled compound of Preparation 9, 0.195 ml (1.4 mmol) of triethylamine and 50 ml of dimethylformamide to provide 234 mg of a white solid which was determined to be 98% pure using HPLC (eluent of 90 acetonitrile in water; 3 ml/min.; λ=280 nm; $R_T$=3.43 min.).

D. Preparation of the compound of formula I where R', R" and R'" are each methyl and $R^{x1}$, $R^{x2}$, $R^{y1}$, $R^{y2}$, $R^{y3}$, $R^{y4}$ and $R^{O}$ are each hydroxy and $R_2$

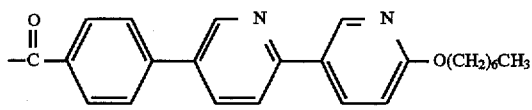

The desired subtitled compound was prepared substantially in accordance with the procedure detailed in Example 1D, using 230 mg (0.45 mmol) of the subtitled compound of Example 4C, 359 mg (0.45 mmol) of the A-30912A nucleus in 15 ml of dimethylformamide to provide 371 mg of a solid which was determined to be 94% pure using HPLC (eluent of 50% acetonitrile in water containing 0.5% monoammonium phosphoric acid; λ=230 nm; 2 ml/min.; $R_T$=3.91 min.).

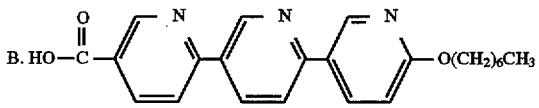

The desired subtitled compound was prepared substantially in accordance with the procedure detailed in Example 1B, using 200 mg (0.49 mmol) of the subtitled compound of Example 5A, 3 ml of a 2N sodium hydroxide solution (6 mmol), 15 ml of dioxane and 6 ml of a 1N hydrochloric acid solution to provide 153 mg of material which was used without further purification.

Yield: 80%.

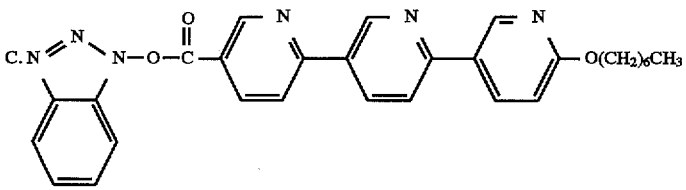

MS(FAB) for $C_{58}H_{75}N_9O_{17}Li$: Calcd: 1176.5441; Found: 1176.5476.

EXAMPLE 5

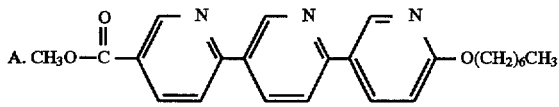

The desired subtitled compound was prepared substantially in accordance with the procedure detailed in Example 3A, using 131 mg (0.14 mmol) of $Pd_2dba_3$, 299 mg (1.14 mmol) of triphenylphosphine, 463 mg (2.7 mmol) of the titled compound of Preparation 1, 1 g (3.18 mmol) of the A solution containing 153 mg (0.39 mmol) of the subtitled compound of Example 5B, 54 mg (0.4 mmol) of the titled compound of Preparation 9, and 83 mg (0.4 mmol) of dicyclohexylcarbodiimide (DCC) in 25 ml of methylene chloride was stirred overnight. The resultant reaction mixture was filtered and then concentrated in vacuo to provide a solid. This solid was slurried in diethyl ether and then filtered to provide 161.3 mg of a solid.

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R^2$ is

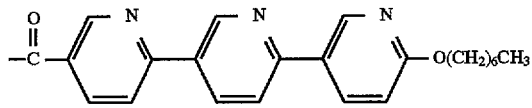

The desired subtitled compound was prepared substantially in accordance with the procedure detailed in Example 1D, using 161 mg (0.24 mmol) of the subtitled compound of Example 5C, 190 mg (0.24 mmol) of the A-30912A nucleus in dimethylformamide to provide 102 mg of a solid which was determined to be 96% pure using HPLC (eluent of 50% acetonitrile in water containing 0.5% monoammonium phosphoric acid; λ=230 nm; 2 ml/min.; $R_T$=3.03 min.). MS(FAB) for $C_{57}H_{74}N_{10}O_{17}Li$: Calcd: 1177.5393; Found: 1177.5350.

EXAMPLE 6

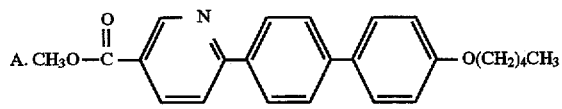

The desired subtitled compound was prepared substantially in accordance with the procedure detailed in Example 2C, using 2.00 g (7.03 mmol) of the subtitled compound of Preparation 5B, 1.51 g (8.80 mmol) of the titled compound of Preparation 1, 0.81 g (0.7 mmol) of palladium tetrakis (triphenylphosphine), 15.8 ml of a 2M solution of sodium carbonate (31.6 mmol), 50 ml of toluene and 20 ml of methanol to provide 0.8856 g of a solid.

Yield: 30%

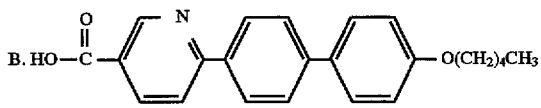

The desired subtitled compound was prepared substantially in accordance with the procedure detailed in Example 1B, using 0.8586 g (2.286 mmol) of the subtitled compound of Example 6A, 6 ml of a 2N sodium hydroxide solution (12 mmol), 228 ml of dioxane and 12 ml of a 1N hydrochloric acid solution to provide 0.65 g of material that was used without further purification.

Yield: 78%.

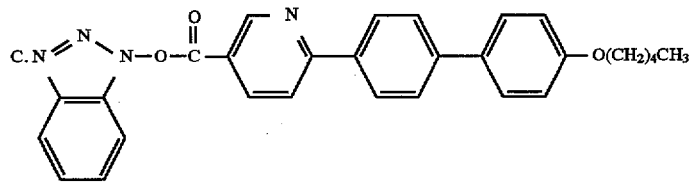

The desired subtitled compound was prepared substantially in accordance with the procedure detailed in Example 1C, using 0.65 g (1.8 mmol) of the subtitled compound of Example 6B, 405 mg (1.90 mmol) of the titled compound of Preparation 9, 0.27 ml (1.94 mmol) of triethylamine and 60 ml of dimethylformamide.

Yield: 624.4 mg (73%).

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R^2$ is

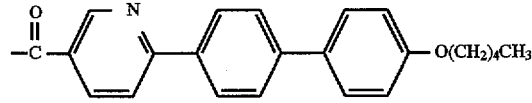

The desired subtitled compound was prepared substantially in accordance with the procedure detailed in Example 1D, using 587.7 mg (1.229 mmol) of the subtitled compound of Example 6C, 893 mg (1.119 mmol) of the A-30912A nucleus in 30 ml of dimethylformamide.

Yield: 542.9 mg (38%).

MS (FAB) for $C_{57}H_{71}N_8O_{16}$: (MH-$H_2O$) Calcd: 1123.4988: Found: 1123.5024.

EXAMPLE 7

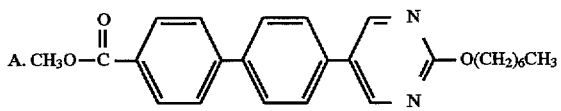

The desired subtitled compound was prepared substantially in accordance with the procedure detailed in Example 3A, using 1.415 g (5.95 mmol) of the subtitled compound of Preparation 6C, 2.75 g (7.63 mmol) of -methoxycarbonyl-4-(4'-trifluorosulfonate)phenyl, 863.3 mg (0.75 mmol) of palladium tetrakis(triphenylphosphine), 13 ml of a 2M solution of sodium carbonate (26 mmol), 50 ml of toluene and 20 ml of methanol to provide 0.5453 g of a solid which was 94% pure by HPLC ($_2$O % water in acetonitrile; λ=280 nm; 3 ml/min.; $R_T$=5.61 min).

Yield: 13%.

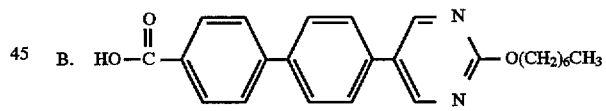

The desired subtitled compound was prepared substantially in accordance with the procedure detailed in Example 1B, using 0.518 g (1.28 mmol) of the subtitled compound of Example 7A, 3.2 ml of a 2N sodium hydroxide solution (6.4 mmol), dioxane and 6.4 ml of a 1N hydrochloric acid solution to provide 458.9 mg of material which was used without further purification.

C. [structure: benzotriazole-N-O-C(O)-biphenyl-pyrimidine-O(CH₂)₆CH₃]

The desired subtitled compound was prepared substantially in accordance with the procedure detailed in Example 1C, using 439.0 mg (1.12 mmol) of the subtitled compound of Example 7B, 251.5 mg (1.18 mmol) of the titled compound of Preparation 9, 0.165 ml (1.18 mmol) of triethylamine and 30 ml of dimethylformamide to provide 309 mg of a solid.

MS(FD): 507.2 (M).

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R^2$ is

[structure: -C(O)-biphenyl-pyrimidine-O(CH₂)₆CH₃]

The desired subtitled compound was prepared substantially in accordance with the procedure detailed in Example 1D, using 300 mg (0.591 mmol) of the subtitled compound of Example 7C, 430.1 mg (0.539 mmol) of the A-30912A nucleus in 15 ml of dimethylformamide to provide 0.3263 g of a white powder which was 98% pure by HPLC (50% acetonitrile in water; λ=230 nm; 2 ml/min; $R_T$=3.22 min).

MS(FAB) for $C_{58}H_{74}N_9O_{16}$: Calcd: 1152.5254: Found: 1152.5247.

EXAMPLE 8

A. [structure: CH₃O-C(O)-phenyl-pyrimidine-phenyl-O(CH₂)₆CH₃]

To a solution containing 4.43 g (10.23 mmol) of the subtitled compound of Preparation 7D and 3.22 g (12.28 mmol) of methyl-4-iodobenzoate in 55 ml of 1,2-dichloroethane, was added 201 mg (0.31 mmol) of bis(triphenylphosphine)palladium (II) chloride, under nitrogen. The resultant reaction mixture was reacted at reflux temperature for approximately forty eight hours. After cooling to room temperature, the reaction mixture was concentrated in vacuo to provide a residue which was slurried in acetonitrile and filtered to provide 1.7135 g of an orangebrown solid.

Yield: 41%.

MS(FD): 404 (M).

B. [structure: HO-C(O)-phenyl-pyrimidine-phenyl-O(CH₂)₆CH₃]

The desired subtitled compound was prepared substantially in accordance with the procedure detailed in Example 1B, using 1.58 g (3.91 mmol) of the subtitled compound of Example 8A, 10.4 ml of a 2N sodium hydroxide solution (20.8 mmol), 250 ml of dioxane and 20.8 ml of a 1N hydrochloric acid solution to provide 1.4133 g of material which was used without further purification.

MS(FD): 390.2.

C. [structure: benzotriazole-N-O-C(O)-phenyl-pyrimidine-phenyl-O(CH₂)₆CH₃]

The desired subtitled compound was prepared substantially in accordance with the procedure detailed in Example 1C, using 352.1 mg (0.902 mmol) of the subtitled compound of Example 8B, 202.2 mg (0.948 mmol) of the titled compound of Preparation 9, 0.13 ml (0.937 mmol) of triethylamine and 30 ml of dimethylformamide to provide 0.294 g of a solid which was used without further purification.

D. Preparation of the compound of formula I where R', R" and R'" are each methyl and $R^{x1}$, $R^{x2}$, $R^{y1}$, $R^{y2}$, $R^{y3}$, $R^{y4}$ and $R^o$ are each hydroxy and $R^2$

[structure: -C(O)-phenyl-pyrimidine-phenyl-O(CH₂)₆CH₃]

The desired subtitled compound was prepared substantially in accordance with the procedure detailed in Example 1D, using 0.2881 g (0.5675 mmol) of the subtitled compound of Example 8C, 0.4116 g (0.516 mmol) of the A-30912A nucleus in 14 ml of dimethylformamide.

Yield: 338.7 mg (51%).

MS(FAB) for $C_{58}H_{74}N_9O_{16}$: Calcd: 1152.5254: Found: 1152.5247.

EXAMPLE 9

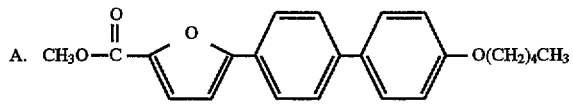

The desired subtitled compound was prepared substantially in accordance with the procedure detailed in Example 2C, using 2.01 g (7.03 mmol) of the subtitled compound of Preparation 5B, 1.51 g (7.3 mmol) of the titled compound of Preparation 8, 816 mg of palladium tetrakis (triphenylphosphine), 2N sodium carbonate, toluene and methanol.

Yield: 1.9961 g (78%).

HPLC: eluent of 80% acetonitrile in water, 2 ml/min; $\lambda$=280 nm; $R_T$=4.64 min.

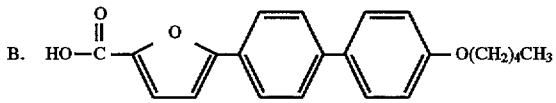

The desired subtitled compound was prepared substantially in accordance with the procedure detailed in Example 1B, using 1.996 g (5.47 mmol) of the subtitled compound of Example 9A, 13.7 ml of a 2N sodium hydroxide solution (27.4 mmol), 200 ml of dioxane and 13.7 ml of a 1N hydrochloric acid solution to provide 2.14 g of a solid.

MS(FD): 351.

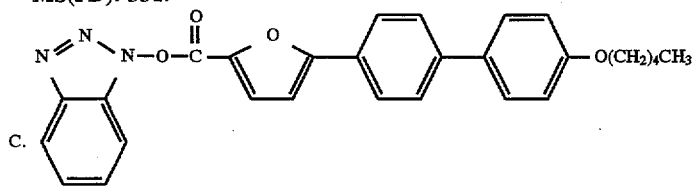

The desired subtitled compound was prepared substantially in accordance with the procedure detailed in Example 1C, using 0.514 mg (1.47 mmol) of the subtitled compound of Example 9B, 0.393 g (1.84 mmol) of the titled compound of Preparation 9, 0.224 ml (1.61 mmol) of triethylamine in dimethylformamide.

Yield: 0.377 g (55%).

MS(FD): 467.

D. Preparation of the compound of formula I where R', R" and R'" are each methyl and $R^{x1}$, $R^{x2}$, $R^{y1}$, $R^{y2}$, $R^{y3}$, $R^{y4}$, and $R^o$ are each hydroxy and $R^2$ is

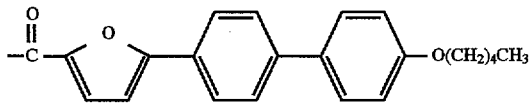

The desired subtitled compound was prepared substantially in accordance with the procedure detailed in Example 1D, using 355 mg (0.76 mmol) of the subtitled compound of Example 9C, 550.4 mg (0.69 mmol) of the A-30912A nucleus in 20 ml of dimethylformamide to provide 223.1 mg of a solid.

MS (FAB) for $C_{56}H_{70}N_7O_{17}$: Calcd: 1112.4828; Found: 1112.4847.

EXAMPLE 10

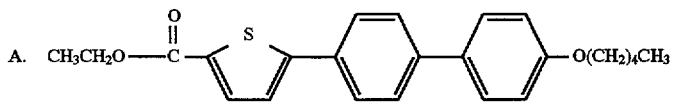

The desired subtitled compound was prepared substantially in accordance with the procedure detailed in Preparation 2C, using 1.50 g (5.28 mmol) of the subtitled compound of Preparation 5B, 1.06 g (5.56 mmol) of 2-ethoxycarbonyl-5-chloro-thiophene, 0.62 g (0.536 mmol) of palladium tetrakis(triphenylphosphine), 48 ml of a 2N solution of sodium carbonate (96 mmol), 39 ml of toluene and 16 ml of methanol to provide 1.6088 g of a solid which was used without further purification.

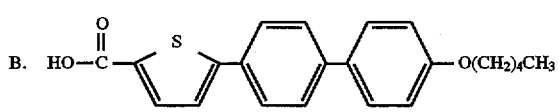

The desired subtitled compound was prepared substantially in accordance with the procedure detailed in Example 1B, using 1.609 g (4.08 mmol) of the subtitled compound of Example 10A, 10.5 ml of a 2N sodium hydroxide solution (21 mmol), 100 ml of dioxane and 21 ml of a 1N hydrochloric acid solution to provide 1.4935 g of a white solid which was used without purification.

MS(FD): 366.

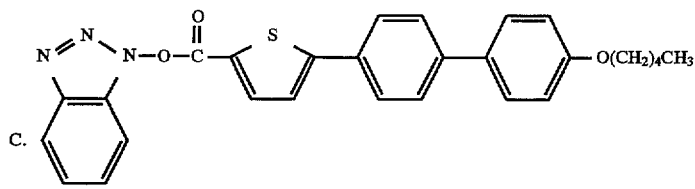

C.

The desired subtitled compound was prepared substantially in accordance with the procedure detailed in Example 1C, using 1.47 g (4.02 mmol) of the subtitled compound of Example 10B, 907 mg (4.25 mmol) of the titled compound of Preparation 9, 0.6 ml (4.37 mmol) of triethylamine in dimethylformamide to provide 1.0498 g of a yellow powder which was used without purification.

D. Preparation of the compound of formula I where R', R" and R'" are each methyl and $R^{x1}$, $R^{x2}$, $R^{y1}$, $R^{y2}$, $R^{y3}$, $R^{y4}$, and $R^o$ are each hydroxy and $R^2$ is

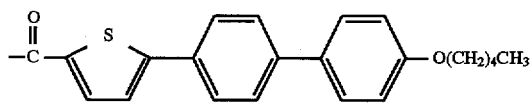

The desired subtitled compound was prepared substantially in accordance with the procedure detailed in Example 1D, using 1.043 g (2.15 mmol) of the subtitled compound of Example 10C, 1.56 g (1.96 mmol) of the A-30912A nucleus in dimethylformamide.

Yield: 2.4611 g.

MS(FAB) for $C_{56}H_{70}N_7O_{16}S$: Calcd: 1128.4600; Found: 1128.4626.

toluene, and 2 ml of methanol to provide 190 mg of a light-brown solid which was used without further purification.

MS(FD): 404.1

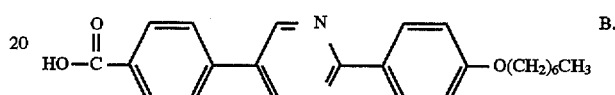

B.

The desired subtitled compound was prepared substantially in accordance with the procedure detailed in Example 1B, using 190 mg (0.47 mmol) of the subtitled compound of Example 11A, 2.5 ml of a 1N sodium hydroxide solution (2.5 mmol), 33 ml of dioxane, and 2.5 ml ol a 1N hydrochloride acid solution to provide 165.3 mg of crude material which was used without further purification.

MS(FD): 390.

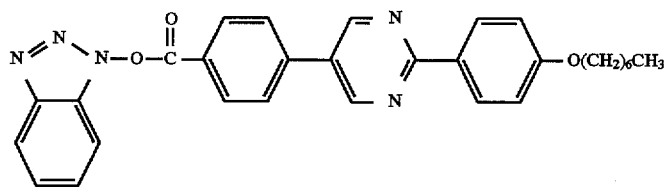

C.

EXAMPLE 11

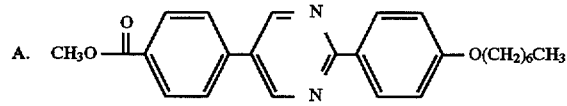

A.

The desired subtitled compound was prepared substantially in accordance with the procedure detailed in Preparation 2C, using 150.6 mg (0.64 mmol) of the subtitled compound of Preparation 7B, 194.6 mg (0.78 mmol) of the subitled compound of Preparation 11B, 73.4 mg (0.06 mmol) of palladium tetrakis(triphenylphosphine), 1.5 ml of a 2M solution of sodium carbonate (3 mmol), 5 ml of The desired subtitled compound was prepared substantially in accordance with the procedure detailed in Example 1C, using 150.4 mg (0.305 mmol) of the subtitled compound of Example 11B, 86.7 mg (0.407 mmol) of the titled compound of Preparation 9, 57 μl (0.415 mmol) of triethylamine in dimethylformamide to provide 73.3 mg of a light-brown solid which was used without further purification.

D. Preparation of the compound of formula I where R', R" and R'" are each methyl and $R^{x1}$, $R^{x2}$, $R^{y1}$, $R^{y2}$, $R^{y3}$, $R^{y4}$, and $R^0$ are each hydroxy and $R^2$ is

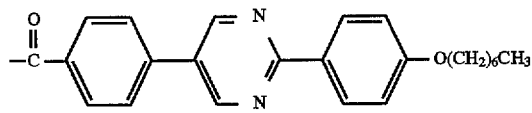 D.

The desired subtitled compound was prepared substantially in accordance with the procedure detailed in Example 1D, using 60.1 mg (0.118 mmol) of the subtitled compound of Example 11C, 86.5 mg (0.108 mmol) of the A-30912A nucleus in 3.5 ml of dimethylformamide to provide 54.1 mg of a white powder.

MS(FAB) for $C_{58}H_{74}N_9O_{16}$: Calcd: 1152.5254; Found: 1152.5236.

EXAMPLE 12

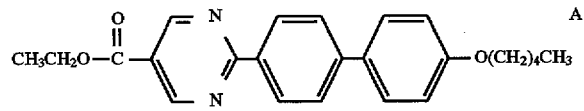 A.

The desired subtitled compound was prepared substantially in accordance with the procedure detailed in Example 3A, using 1.04 g (3.66 mmol) of the subtitled compound of Preparation 5B, 0.75 g (4.02 mmol) of the subtitled compound of Preparation 12D, 0.375 g (0.32 mmol) of palladium tetrakis(triphenylphosphine), 8 ml of a 2M solution of sodium carbonate (16 mmol), 26 ml of toluene and 10 ml of methanol.

Yield: 0.6678 g (47%).

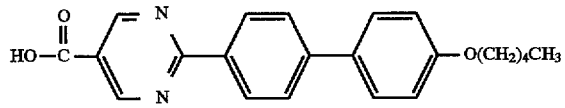 B.

The desired subtitled compound was prepared substantially in accordance with the procedure detailed in Example 1B, using 559.3 mg (1,432 mmol) of the subtitled compound of Example 12A, 7.2 ml of 2N sodium hydroxide (7.2 mmol), 90 ml of dioxane and 1N hydrochloric acid.

Yield: 167.1 mg (92%).

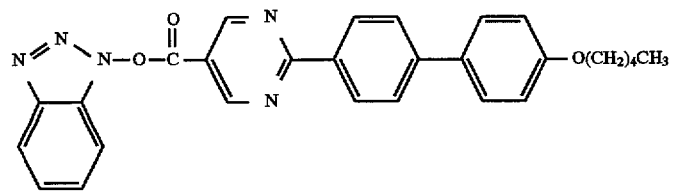

The desired subtitled compound was prepared substantially in accordance with the procedure detailed in Example 1C, using 154.5 mg (0.426 mol) of the subtitled compound of Example 12B, 97.6 mg (0.458 mmol) of the titled compound of Preparation 9, 0.06 ml (0.431 mmol) of triethylamine and 14 ml of dimethylformamide.

Yield: 100 mg (49%).

D. Preparation of the compound of formula I where R', R" and R'" are each methyl and $R^{x1}$, $R^{x2}$, $R^{y1}$, $R^{y2}$, $R^{y3}$, $R^{y4}$, and $R^0$ are each hydroxy and $R^2$ is

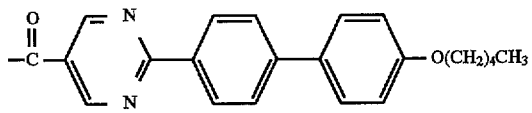

The desired subtitled compound was prepared substantially in accordance with the procedure detailed in Example 1D, using 100 mg (0.208 mmol) of the subtitled compound of Example 12C, 158 mg (0.198 mmol) of the A-30912A nucleus in dimethylformamide to provide 11.8 mg of the desired compound.

MS(FAB) for $C_{56}H_{70}N_9O_{16}$ ($M-H_2O$): Calcd: 1124.4941: Found: 1124.4919.

The compounds of formula I exhibit antifungal and antiparasitic activity. For example, the compounds of formula I inhibit the growth of various infectious fungi including Candida spp. such as *C. albicans*, *C. parapsilosis*, *C. krusei*, *C. glabrata*, or *C. tropicalis*, *C. lusitaniae*; Torulopus spp. such as *T. glabrata*; Aspergillus spp. such as *A. fumigatus*; Histoplasma spp. such as *H. capsulatum*; Cryptococcus spp. such as *C. neoformans*; Blastomyces spp. such as *B. dermatitidis*; Fusarium spp., Trichophyton spp., *Pseudallescheria boydii*, *Coccidioides immitis*, *Sporothrix schenckii* and the like.

Antifungal activity of a test compound was determined in vitro by obtaining the minimum inhibitory concentration (MIC) of the compound using a standard agar dilution test or a disc-diffusion test. The compound was then tested in vivo (in mice) to determine the effective dose of the test compound for controlling a systemic fungal infection.

Accordingly, the following compounds were tested for antifungal activity against *C. albicans*.

TABLE 1

| Minimal inhibitory concentration against *C. albicans* | |
|---|---|
| Example No. | MIC (µg/ml) |
| 1D | 0.78 |
| 2D | 0.039 |
| 3D | 0.02 |
| 4D | 0.002 |

TABLE 1-continued

Minimal inhibitory concentration against *C. albicans*

| Example No. | MIC (μg/ml) |
| --- | --- |
| 5D | 0.01 |
| 6D | 0.02 |
| 7D | 0.01 |
| 8D | 0.005 |
| 9D | 0.312 |
| 10D | 0.078 |
| 11D | 0.039 |
| 12D | 0.02 |

In addition, the effective dose of the following compounds for controlling a systemic fungal infection (*C. albicans*) was tested in vivo (mice).

TABLE 2

$ED_{50}$ (mouse, i.p.)

| Example No. | $ED_{50}$ (mg/kg) |
| --- | --- |
| 1D | 1.57 |
| 2D | 1.25 |
| 3D | 0.31 |
| 4D | 0.41 |
| 5D | 1.13 |
| 6D | 0.31 |
| 7D | 0.47 |
| 8D | 0.31 |
| 9D | >2.5 |
| 10D | 5.52 |
| 11D | 0.38 |

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cryptosporidium spp., Isospora spp., Cyclospora spp., Trichomonas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2-3 days to about 2-3 weeks or longer.

A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal, or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mp/capsule) |
|---|---|
| Active ingredient | 250 |
| Starch, dried | 200 |
| Magnesium stearate | 10 |
| Total | 460 mg |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism *Pneumocystis carinii*, or alternatively they can be used to treat a host that has been infected with *P. carinii*. A compound of formula I may be administered parenterally, for example using intramuscular, intravenous or intra-peritoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:
1. A compound of formula I

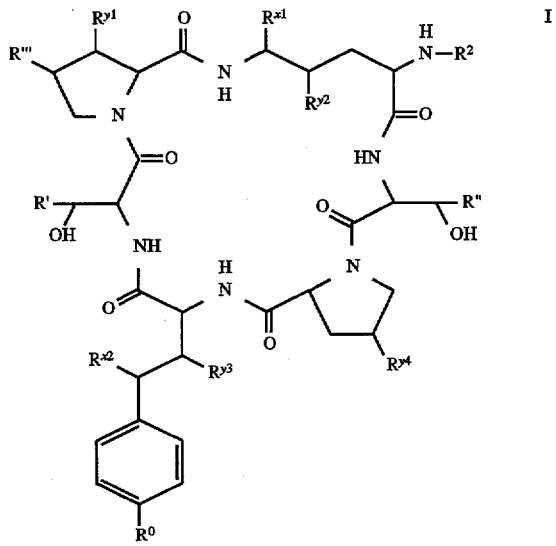

wherein:

R' is hydrogen, methyl, —CH$_2$CH$_2$NH$_2$ or —CH$_2$C(O)NH$_2$;

R" and R'" are independently methyl or hydrogen;

R$^{x1}$ is hydrogen, hydroxy, —NH—R, or —O—R;

R is C$_1$–C$_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$)alkyl;

a, b and c are independently 1, 2, 3, 4, 5 or 6;

R$^{z1}$ and R$^{z2}$ are independently hydrogen, C$_1$–C$_6$ alkyl, or R$^{z1}$ and R$^{z2}$ combine to form —CH$_2$(CH$_2$)$_e$CH$_2$—;

R$^{z3}$ and R$^{z4}$ are independently hydroxy or C$_1$–C$_6$ alkoxy;

d is 1 or 2;

e is 1, 2 or 3;

R$^{x2}$, R$^{y1}$, R$^{y2}$, R$^{y3}$ and R$^{y4}$ are independently hydroxy or hydrogen;

R$^0$ is hydroxy, —OP(O)(OH)$_2$ or a group of the formula:

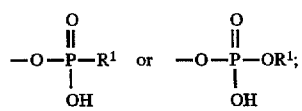

R$^1$ is C$_1$–C$_6$ alkyl, phenyl, p-halo-phenyl, p-nitrophenyl, benzyl, p-halo-benzyl or p-nitro-benzyl;

R$^2$ is

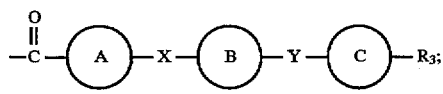

A, B, and C are independently selected from the following groups:

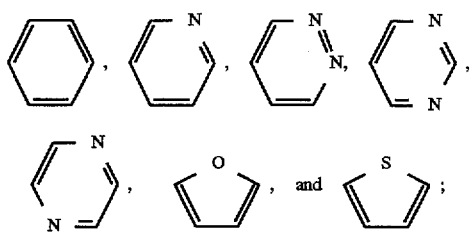

X and Y are independently a bond or —C≡C—;

R³ is C₁–C₁₂ alkyl, C₁–C₁₂ alkoxy or —O—(CH₂)$_m$—[O—(CH₂)$_n$]$_p$—O—(C₁–C₁₂ alkyl);

m is 2, 3 or 4;

n is 2, 3 or 4; and p is 0 or 1;

with the proviso that A, B, and C cannot all be

or a pharmaceutically acceptable salt thereof.

2. A compound according to claim 1 where:

R', R" and R'" are each methyl;

R$^{y1}$, R$^{y2}$, R$^{y3}$ and R$^{y4}$ are each hydroxy;

R$^{x1}$ is hydrogen, hydroxy or —O—R;

R is methyl, benzyl, —CH₂CHOHCH₂OH, —(CH₂)$_b$NR$^{z1}$R$^{z2}$ or —(CH₂)₂POR$^{z3}$R$^{z4}$;

b is 2, 3, 4, 5 or 6;

R$^{z1}$ and R$^{z2}$ are independently hydrogen or C₁–C₄ alkyl;

R$^{z3}$ and R$^{z4}$ are independently hydroxy or methoxy;

R$^{x2}$ is hydrogen or hydroxy;

R° is hydroxy, —OP(O)(OH)₂ or a group of the formula:

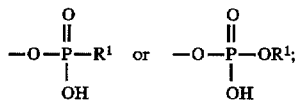

R¹ is methyl;

or a pharmaceutically acceptable salt thereof.

3. A compound according to claim 2 where:

R$^{x1}$ is hydrogen or hydroxy;

R$^{x2}$ is hydrogen or hydroxy;

R° is hydroxy;

R³ is C₁–C₁₂ alkoxy or —O—(CH₂)₂—O—(C₁–C₁₂ alkyl);

or a pharmaceutically acceptable salt thereof.

4. A compound according to claim 3 where:

R$^{x1}$ is hydroxy;

R$^{x2}$ is hydroxy;

X and Y are a bond;

R³ is C₁–C₈ alkoxy;

or a pharmaceutically acceptable salt thereof.

5. A compound according to claim 4 where:

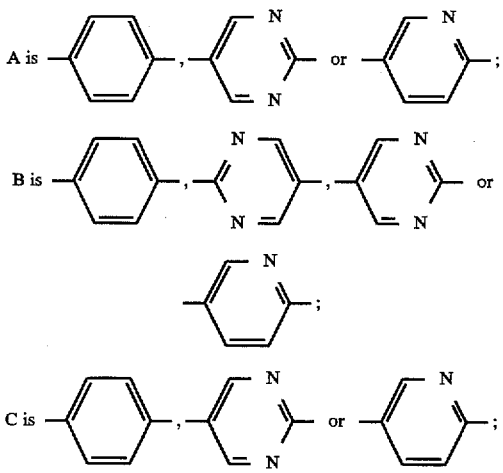

or a pharmaceutically acceptable salt thereof.

6. A pharmaceutical formulation comprising one or more pharmaceutically acceptable carriers, diluents or excipients and a compound of claim 1.

7. A pharmaceutical formulation according to claim 6 where the compound is one where:

R', R" and R'" are each methyl;

R$^{y1}$, R$^{y2}$, R$^{y3}$ and R$^{y4}$ are each hydroxy;

R$^{x1}$ is hydrogen, hydroxy or —O—R;

R is methyl, benzyl, —CH₂CHOHCH₂OH, —(CH₂)$_b$NR$^{z1}$R$^{z2}$ or —(CH₂)₂POR$^{z3}$R$^{z4}$;

b is 2, 3, 4, 5 or 6;

R$^{z1}$ and R$^{z2}$ are independently hydrogen or C₁–C₄ alkyl;

R$^{z3}$ and R$^{z4}$ are independently hydroxy or methoxy;

R$^{x2}$ is hydrogen or hydroxy;

R° is hydroxy, —OP(O)(OH)₂ or a group of the formula:

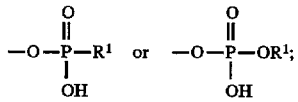

R¹ is methyl;

or a pharmaceutically acceptable salt thereof.

8. A pharmaceutical formulation according to claim 7 where the compound is one where:

R$^{x1}$ is hydrogen or hydroxy;

R$^{x2}$ is hydrogen or hydroxy;

R° is hydroxy;

R³ is C₁–C₁₂ alkoxy or —O—(CH₂)₂—O—(C₁–C₁₂ alkyl);

or a pharmaceutically acceptable salt thereof.

9. A pharmaceutical formulation according to claim 8 where the compound is one where:

R$^{x1}$ is hydroxy;

R$^{x2}$ is hydroxy;

X and Y are a bond;

R³ is C₁–C₈ alkoxy;

or a pharmaceutically acceptable salt thereof.

10. A pharmaceutical formulation according to claim 9 where the compound is one where:

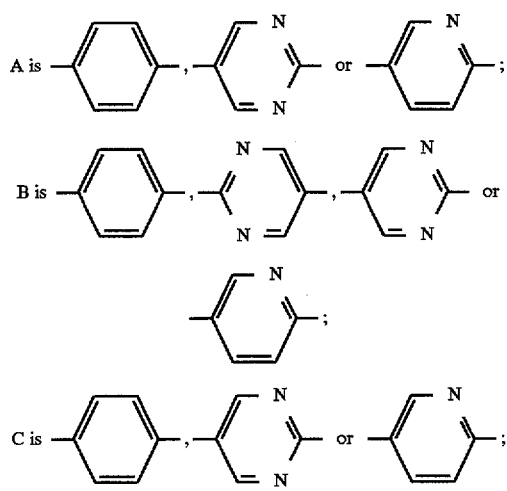

or a pharmaceutically acceptable salt thereof.

11. A method of inhibiting fungal activity comprising contacting a compound of claim 1 with a fungus.

12. A method according to claim 11 where the compound is one where:

R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;
$R^0$ is hydroxy, —OP(O)(OH)$_2$ or a group of the formula:

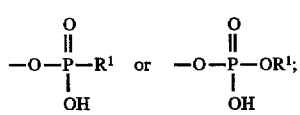

$R^1$ is methyl;
or a pharmaceutically acceptable salt thereof.

13. A method according to claim 12 where the compound is one where:

$R^{x1}$ is hydrogen or hydroxy;
$R^{x2}$ is hydrogen or hydroxy;
$R^0$ is hydroxy;
$R^3$ is $C_1$–$C_{12}$ alkoxy or —O—(CH$_2$)$_2$—O—($C_1$–$C_{12}$ alkyl);
or a pharmaceutically acceptable salt thereof.

14. A method according to claim 13 where the compound is one where:

$R^{x1}$ is hydroxy;
$R^{x2}$ is hydroxy;
X and Y are a bond;
$R^3$ is $C_1$–$C_8$ alkoxy;
or a pharmaceutically acceptable salt thereof.

15. A method according to claim 14 where the compound is one where:

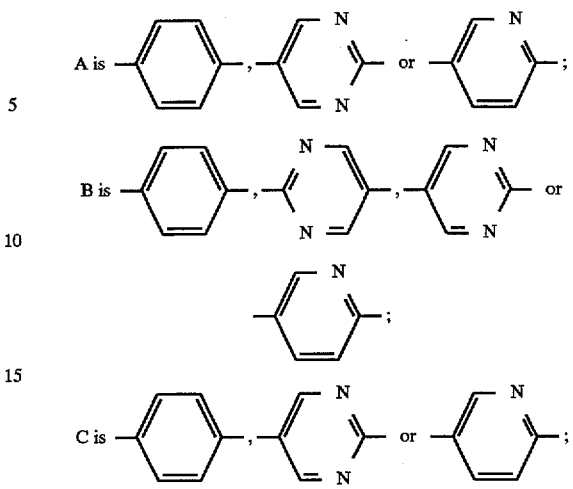

or a pharmaceutically acceptable salt thereof.

16. A method of treating a fungal infection which comprises administering an effective amount of a compound of claim 1 to a host in need of such treatment.

17. A method according to claim 16 where the compound is one where:

R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;
$R^0$ is hydroxy, —OP(O)(OH)$_2$ or a group of the formula:

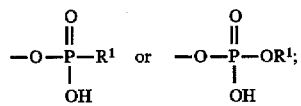

$R^1$ is methyl;
or a pharmaceutically acceptable salt thereof.

18. A method according to claim 17 where the compound is one where:

$R^{x1}$ is hydrogen or hydroxy;
$R^{x2}$ is hydrogen or hydroxy;
$R^0$ is hydroxy;
$R^3$ is $C_1$–$C_{12}$ alkoxy or —O—(CH$_2$)$_2$—O—($C_1$–$C_{12}$ alkyl);
or a pharmaceutically acceptable salt thereof.

19. A method according to claim 18 where the compound is one where:

$R^{x1}$ is hydroxy;
$R^{x2}$ is hydroxy;
X and Y are a bond;
$R^3$ is $C_1$–$C_8$ alkoxy;
or a pharmaceutically acceptable salt thereof.

20. A method according to claim 19 where the compound is one where:

A is 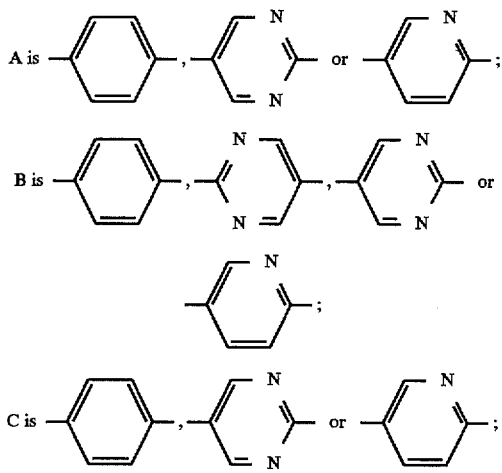

B is

C is or a pharmaceutically acceptable salt thereof.

21. A method for inhibiting parasitic activity comprising contacting a compound of claim 1 with a parasite.

22. A method according to claim 21 where the compound is one where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;

$R^{x2}$ is hydrogen or hydroxy;

$R^o$ is hydroxy, —OP(O)(OH)$_2$ or a group of the formula:

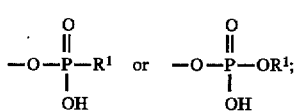

$R^1$ is methyl;

or a pharmaceutically acceptable salt thereof.

23. A method according to claim 22 where the compound is one where:

$R^{x1}$ is hydrogen or hydroxy;

$R^{x2}$ is hydrogen or hydroxy;

$R^o$ is hydroxy;

$R^3$ is $C_1$–$C_{12}$ alkoxy or —O—(CH$_2$)$_2$—O—($C_1$–$C_{12}$ alkyl);

or a pharmaceutically acceptable salt thereof.

24. A method according to claim 23 where the compound is one where:

$R^{x1}$ is hydroxy;

$R^{x2}$ is hydroxy;

X and Y are a bond;

$R^3$ is $C_1$–$C_8$ alkoxy;

or a pharmaceutically acceptable salt thereof.

25. A method according to claim 24 where the compound is one where:

A is 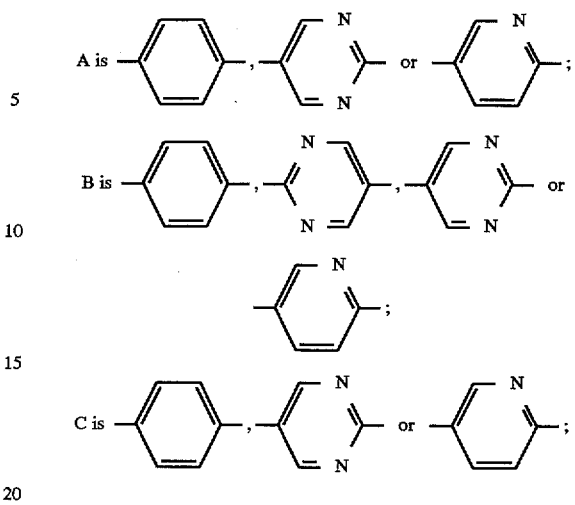

B is

C is or a pharmaceutically acceptable salt thereof.

26. A method for treating or preventing the onset of Pneumocystis pneumonia in a host susceptible to Pneumocystis pneumonia which comprises administering an effective amount of a compound of formula I of claim 1, or a pharmaceutically acceptable salt thereof, to a host in need of such treatment.

27. A method according to claim 26 where the compound is one where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;

$R^{x2}$ is hydrogen or hydroxy;

$R^o$ is hydroxy, —OP(O)(OH)$_2$ or a group of the formula:

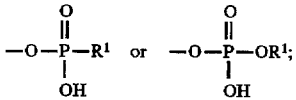

$R^1$ is methyl;

or a pharmaceutically acceptable salt thereof.

28. A method according to claim 27 where the compound is one where:

$R^{x1}$ is hydrogen or hydroxy;

$R^{x2}$ is hydrogen or hydroxy;

$R^o$ is hydroxy;

$R^3$ is $C_1$–$C_{12}$ alkoxy or —O—(CH$_2$)$_2$—O—($C_1$–$C_{12}$ alkyl);

or a pharmaceutically acceptable salt thereof.

29. A method according to claim 28 where the compound is one where:

$R^{x1}$ is hydroxy;

$R^{x2}$ is hydroxy;

X and Y are a bond;

$R^3$ is $C_1$–$C_8$ alkoxy;

or a pharmaceutically acceptable salt thereof.

30. A method according to claim 29 where the compound is one where:

A is 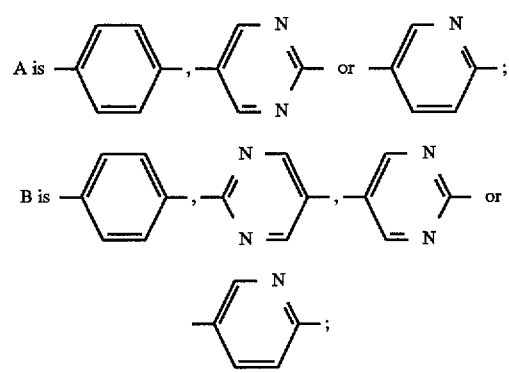
B is 
C is 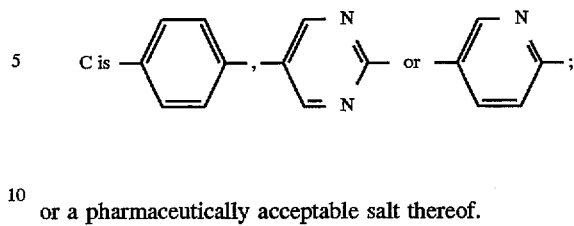
or a pharmaceutically acceptable salt thereof.
* * * * *

UNITED STATES PATENT AND TRADEMARK OFFICE
CERTIFICATE OF CORRECTION

PATENT NO. : 5,693,611
DATED : December 2, 1997
INVENTOR(S) : Stacy Kay Henle et al.

It is certified that error appears in the above-identified patent and that said Letters Patent is hereby corrected as shown below:

Column 30, Line 39, "HPLC $_2$0% water" should read --HPLC (20% water--

Signed and Sealed this

Eighth Day of September, 1998

Attest:

BRUCE LEHMAN

Attesting Officer          Commissioner of Patents and Trademarks